United States Patent [19]
Habener et al.

[11] Patent Number: 5,858,973
[45] Date of Patent: Jan. 12, 1999

[54] TRANSCRIPTION FACTOR AND USES THEREFOR

[75] Inventors: Joel F. Habener, Newton Highlands; Christopher P. Miller, Arlington, both of Mass.

[73] Assignee: The General Hospital Corporation, Boston, Mass.

[21] Appl. No.: 202,044

[22] Filed: Feb. 23, 1994

[51] Int. Cl.$^6$ .......................... A61K 38/00; A61K 38/16; A61K 38/31
[52] U.S. Cl. .............................. 514/12; 530/358; 530/311
[58] Field of Search .............................. 514/12; 530/358, 530/311

[56] References Cited

U.S. PATENT DOCUMENTS 5,240,911  8/1993  Totsuka et al. ............................ 514/12

OTHER PUBLICATIONS

C.P. Miller et al., Abstract: "IDX–1: A New Homeodomain Transcription Factor Expressed in Rat Islets and Duodenum", *75th Annual Meeting of The Endocrine Society*, Las Vegas, Nevada, Jun. 1993.

Ohlsson et al., "IPF1, a Homeodomain Containing Transactivator of the Insulin Gene", *The EMBO Journal* 12:4251–4259, No. 11, Nov. 1993.

Leonard et al., "Characteriztion of Somatostatin Transactivation Factor–1, a Novel Homeobox Factor that Stimulates Somatosttin Expression in Pancreatic Islet Cells", *Molecular Endocrinology* 7:1275–1283, Oct. 1993.

C.P. Miller et al., "IDX–1: A New Homeodomain Transcription Factor Expressed in Rat Pancreatic Islets and Duodenum that Transactivated the Somatostatin Gene", *The EMBO Journal 13*, No. 4, 1994.

Leonard et al., "*Characterization of STF–1, A Novel Homeodomain Factor Which Cooperates With Creb to Stimulate Somatostatin Expression in Pancreatic Islet Cells*", The Clayton Foundation Laboratories for Peptide Biology, The Salk Institute for Biological Studies, La Jolla, CA, Jun. 1993.

*Primary Examiner*—Robert A. Wax
*Assistant Examiner*—Lisa J. Hobbs
*Attorney, Agent, or Firm*—Banner & Allegretti, Ltd.

[57] ABSTRACT

The invention features a novel recombinant polypeptide that transactivates the somatostatin promoter, the polypeptide being present in pancreatic duct cells and not present in pancreatic α-cells, the polypeptide being encoded by a gene which encodes a protein on the order of 31 kd.

6 Claims, 16 Drawing Sheets

```
                                                                           61
GAATTCCGGGGCGCTGAGAGTCCGTGAGCTGCCCAGCGCCTAAGGCCTGGCTTGTAGCTCC

M  N  S  E  E  Q  Y  Y    8
CTACCCCGGGCTGCCGGCCCCGAAGTGCCGGCTGCCACCATGAATAGTGAGGAGCAGTACT        122

A  A  T  Q  L  Y  K  D  P  C  A  F  Q  R  G  P  V  P  E  F       28
ACGCGGCCACACAGCTCTACAAGGACCCGTGCGCATTCCAGAGGGGTCCGGTGCCAGAGTT        183

S  A  N  P  P  A  C  L  Y  M  G  R  Q  P  P  P  P  P  T  P       49
CAGTGCTAATCCCCCTGCGTGCCTGTACATGGGCCGCCAGCCCCCACCTCCGCCGACACCC        244

Q  F  A  G  S  L  G  T  L  E  Q  G  S  P  P  D  I  S  P  Y  E       69
CAGTTTGCAGGCTCGCTGGGAACGCTGGAACAGGGAAGTCCCCGGACATCTCCCCATACG        305

V  P  P  L  A  D  D  P  A  G  A  H  L  H  H  H  L  P  A  Q       89
AAGTGCCCCCGCTCGCCGATGACCCGGCTGGCGCGCACCTCCACCACCACCTCCCAGCTCA       366

L  G  L  A  H  P  P  P  G  P  F  P  N  G  T  E  T  G  G  L      110
GCTCGGGCTCGCCCATCCACCTCCCGGACCTTTCCCGAATGGAACCGAGACTGGGGGCCTG       427

E  E  P  S  R  V  H  L  P  F  P  W  M  K  S  T  K  A  H  A  W      130
GAAGAGCCCAGCCGCGTTCATCTCCCTTTCCCGTGGATGAAATCCACCAAAGCTCACGCGT       488

K  S  Q  W  A  G  G  A  Y  A  A  E  P  E  E  N  K  R  T  R      150
GGAAAAGCCAGTGGGCAGGAGGTGCATACGCAGCAGAACCGGAGGAGAATAAGAGGACCCG       549

T  A  Y  T  R  A  Q  L  L  E  L  E  K  E  F  L  F  N  K  Y      171
TACAGCCTACACTCGGGCCCAGCTGCTGGAGCTGGAGAAGGAATTCTTATTTAACAAATAC       610

I  S  R  P  R  R  V  E  L  A  V  M  L  N  L  T  E  R  H  I  K   191
ATCTCCCGGCCTCGCCGGGTGGAGCTGGCAGTGATGCTCAACTTGACTGAGAGACACATCA       671

I  W  F  Q  N  R  R  M  K  W  K  K  E  E  D  K  K  R  S  S   211
AAATCTGGTTCCAAAACCGTCGCATGAAGTGGAAGAAAGAGGAAGATAAGAAACGTAGTAG       732

G  T  T  S  G  G  G  G  E  E  P  E  Q  D  C  A  V  T  S         232
CGGGACAACGAGCGGGGGCGGTGGGGGCGAAGAGCCGGAGCAGGATTGTGCCGTAACCTCG       793

G  E  E  L  L  A  L  P  K  P  P  P  P  G  G  V  V  P  S  G  V  252
GGCGAGGAGCTGCTGGCATTGCCAAAGCCACCACCTCCCGGAGGTGTTGTGCCCTCAGGCG       854

P  A  A  A  R  E  G  R  L  P  S  G  L  S  A  S  P  Q  P  S   272
TCCCTGCTGCTGCCCGGGAGGGCCGACTGCCTTCCGGCCTTAGTGCGTCCCCACAGCCCTC       915

S  I  A  P  L  R  P  Q  E  P  R  *                              283
CAGCATCGCGCCACTGCGACCGCAGGAACCCCGGTGAGGACCGCAGGCTGAGGGTGAGCGG       976

GTCTGGGACCCAGAGTGCGGACATGGGCATGGGCCCGGGCAGCTGGATAAGGGAGGGGATC      1037
ATGAGGCTTAACCTAAACGCCACACACAAGGAGAACATTCTTCTTGGGGGCACAAGAGCCA      1098
GTTGGGTATACCAGCGAGATGCTGGCAGACCTCTGGGAAAAAAAAGACCCGAGCTTCTGA      1159
AAACTTTGAGGCTGCCTCTCGTGCCATGTGAACCGCCAGGTCTGCCTCTGGGACTCTTTCC      1220
TGGGACCAATTTAGAGAATCAGGCTCCCAACTGAGGACAATGAAAAGGTTACAAACTTGAG      1281
CGGTCCCATAACAGCCACCAGGCGAGCTGGACCGGGTGCCTTTGACTGGTCGGCCGAGCAA      1342
TCTAAGGTTGAGAATAAAGGGAGCTGTTTGAGGTTTCAAAAAAAAAAAAAAACCGGAATTC      1404
```

FIG. 1A

|  | Helix 1 | Helix 2 | Helix 3 |
|---|---|---|---|

```
              |         |         |         |         |         |
              10        20        30        40        50        60
              |         |         |         |         |         |
Antp     ERKRGRQTYTRYQTI ELEKEFHFNRYLTRRRRIEIAHALCLTERQIKIWFQNRRMKWKKEN IDX-1    -N--T-TA---A-L----------L--K-IS-P--V-L-VM-N----H-------------E
XlHbox8  ----------------------L--K-IS-P--V-L-VM-N----H-------------E
Htr-A2   N--T-TA-S-S-L---------DK-IS-P--V-L-SS-N----H--------------ME XlHbox1  D-R----I-S-----------------------N---------------------------S
Hox1.4   -P--S-TA---Q-V-------------------T---S--V----------------DH
Hox1.6   QPNAV-TNF-TK-LT------K----A--V---AS-Q-N-T-V-----------Q--RE
Hox2.6   -P--S-TA---Q-V-------Y--------V--------S-----------------DH
Cdx-3    TKDKY-VV--DH-R-------YS--I-I--KA-L-AT-G-S----V--------A-ER-I-
```

FIG. 1C

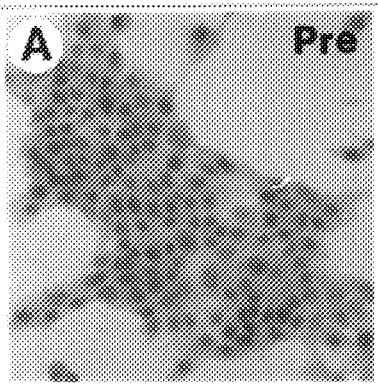 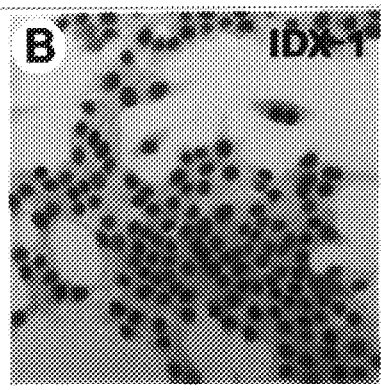 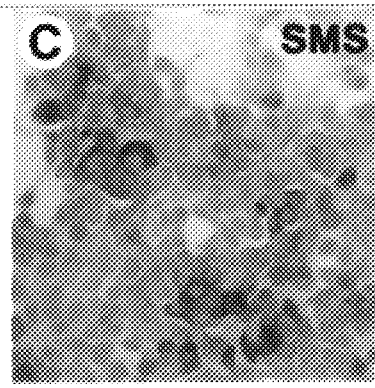
FIG. 4A     FIG. 4B     FIG. 4C
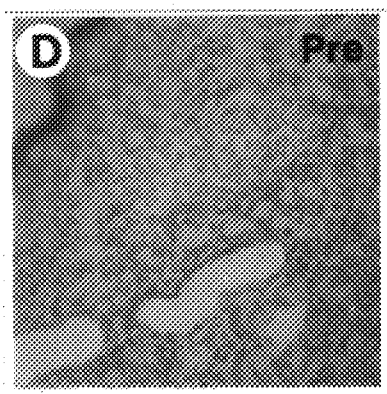 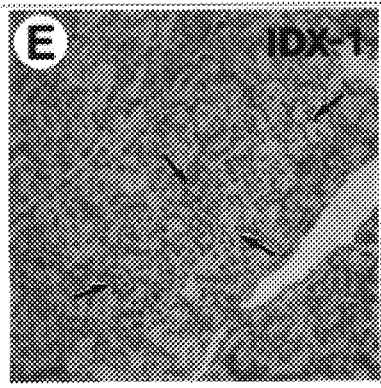 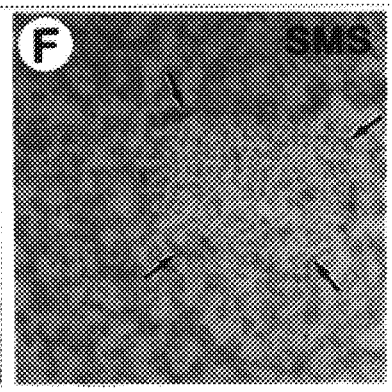
FIG. 4D     FIG. 4E     FIG. 4F
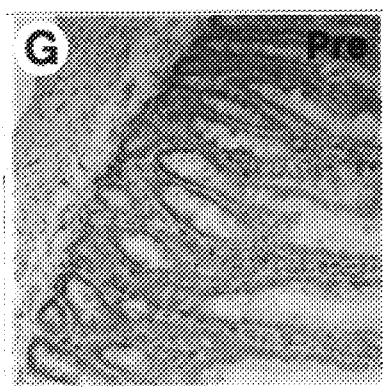 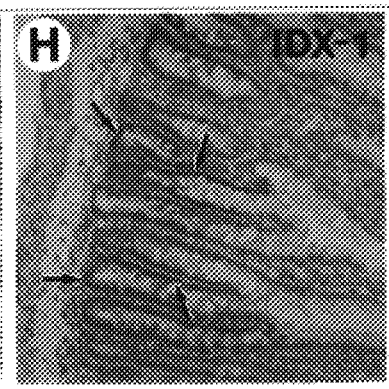 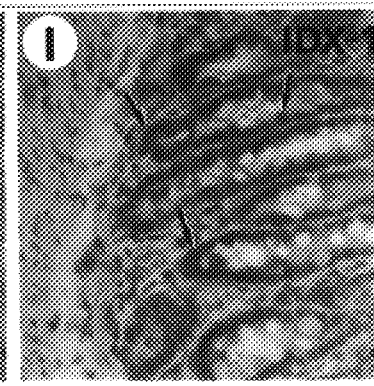
FIG. 4G     FIG. 4H     FIG. 4I

| ELEMENT | SEQUENCE (5'→3') | LOCATION |
|---|---|---|
| SMS-TAAT1 | CTGATTGCATATTAATTCTCAGAT | (-438/-462) |
| SMS-TAAT2 | GATCTGAGTAATTAATCATGCACC | (-280/-303) |
| SMS-UE-B | TTTGCGAGGCTAATGGTGCGTAA | (-83/-106) |
| SMS-PS | AGACCAAATAATCTTGCCTTCACT | (-242/-219) |
| INS1-FLAT | TTGTTAATAATCTAATTACCCTAG | (-209/-233) |

FIG. 6A

| Seq# | Freq. | Antp ELEKEFHFNRYLTRRRIEIAHALCLTERQIKIWFQN (20-30-40-50) | Closest Genbank Matches (aa, na); ref. |
|---|---|---|---|
| 1 | (45/80) | ------L--K-IS-P---V-L-VM-N-----H------ | IDX-1; XlHbox8 (100%, 80%); Wright et al., 1989 |
| 16 | (6/80) | ------C-R-I-I--KS-L-VN-G-S----V------ | Mouse Cdx-4 (100%, 98%); Garner and Wright, 1993 |
| 17 | (2/80) | --------------------T--S---V------ | Mouse Hox1.4 (100%, 95%); Duggal et al., 1987 |
| 19 | (3/80) | ------ETQK--SPPE-KRL-KM-Q-S---V------ | No Significant matches |
| 22 | (1/80) | ------CKK---SLTE-SQ-----K-S-V-V------ | CHox7 (100%, 98%); Fainsod and Gruenbaum, 1989 |
| 24 | (6/80) | -------Y---------V------S--------- | Mouse Hox2.6 (100%, 97%); Graham et al., 1988 |
| 27 | (4/80) | ------YS--I---KA-L-AT-G-S----V------ | Hamster Cdx-3 (100%, 92%); German et al., 1992 |
| 35 | (5/80) | ------YS--I---KS-L-AN-G-----V------ | Mouse Cdx-1 (100%, 92%); Duprey et al., 1988 |
| 39 | (3/80) | ------L--P-----K----VS-T-G-----V------ | Mouse Hox4.3 (100%, 99%); Nazarali et al., 1992 |
| 43 | (2/80) | ---------K--C-P--V---AL-D-----V------ | Rat Hox1.11 (100%, 100%); Patel et al., 1992 |
| 48 | (1/80) | ---------C-P--V-M-NL-N------------ | Mouse Hox-4A (100%, 96%); Lonai et al., 1987 |
| 82 | (1/80) | -------------------------S-------- | Mouse Hox1.3 (100%, 97%); Odenwald et al., 1987 |

----> PCRHD1    <---- PCRHD2

TRANSCRIPTION FACTOR AND USES THEREFOR

FIELD OF THE INVENTION

The invention relates to proteins or polypeptides useful for of the disease Diabetes mellitus. The invention was made with Government funding and, therefore, the U.S. Government has rights in the invention.

BACKGROUND OF THE INVENTION

Diabetes mellitus type I, or insulin-dependent diabetes, results from a genetically conferred vulnerability that causes a primary deficiency of insulin. This deficiency of insulin is believed to be the consequence of destruction of a specialized population of cells that produce insulin in the body, i.e., pancreatic β-cells. An autoimmune process may also contribute to β-cell damage. As a consequence of insulin lack (and glucagon excess), glucose production is augmented, and the efficiency of peripheral glucose use is reduced until a new equilibrium between these processes is reached at a very high plasma glucose level. Because of the high plasma glucose levels, the filtered load of glucose exceeds the renal tubular capacity for reabsorption. Glucose therefore is excreted in the urine in large quantities, causing, by its osmotic effect, increased excretion of water and salts and frequent urination. The goal of insulin treatment is to systemically lower plasma levels of glucose, free fatty acids, and ketoacids to normal and reduce urine nitrogen losses. This result is achieved by direct actions of insulin and also by diminishing the secretion of the insulin antagonist glucagon.

Another more common form of diabetes mellitus, noninsulin-dependent or type II, often is associated with obesity. In this disease, there appears to be both a deficit of insulin production (Weir et al., 1982, Amer. Jour. Med. 73:461) in combination with a resistance to the action of insulin on major target tissues. The locus of resistance is distal to the insulin receptor binding site, but defects in receptor tyrosine kinase activity, glucose transport, and activities of insulin-sensitive enzymes have been found. In addition, there is a derangement in β-cell recognition of glucose as a stimulus, so that first phase insulin secretion is lost, though a delayed release does occur. Treatment of type II diabetes does not normally require insulin administration. Caloric regulation, weight reduction if obesity is present, and use of sulfonylurea drugs simultaneously improve tissue responsiveness to endogenous insulin and β-cell responsiveness to glucose. In late stages, insulin administration is usually required.

Insulin excess is usually caused by tumors of the β-cells. The cardinal manifestation is a low plasma glucose level in the fasting state. With chronic insulin excess and persistent hypoglycemia, disturbed central nervous system function results in bizarre behavior, defects in cerebration, loss of consciousness, or convulsions. Removal of the tumor may cure the condition. Alternatively, drugs that inhibit insulin secretion may ameliorate the condition.

It is an object of the invention to provide a nucleic acid sequence encoding a novel transcriptional activator that is present in certain pancreatic cell populations, and the encoded transcriptional activator.

Another object of the invention is to provide an in vitro method for producing a desired protein using the novel transcriptional activator to activate transcription of the gene encoding the desired protein.

Yet another object of the invention is to provide methods of treating Diabetes mellitus type I, type II, or diseases in which insulin is produced in excess.

Another object of the invention is to provide a transgenic mouse model for diabetes, in which expression of the novel transcriptional activator is altered.

These and further objects of the invention will be apparent for one skilled in the art.

SUMMARY OF THE INVENTION

The invention features a novel recombinant polypeptide, i.e., IDX-1 or a variant thereof, that transactivates the somatostatin promoter, the polypeptide being present in pancreatic duct cells and not present in pancreatic α-cells. The polypeptide is encoded by a gene which encodes a protein on the order of 31 kd. As used herein, "transactivates" means to activate or aid in activating transcription of a gene associated with the promoter: "present" means expressed from a gene that is active in such cells.

The invention also encompasses a nucleic acid sequence encoding IDX-1 or its variant, replicable expression vectors comprising and capable of expressing the nucleic acid sequence in a transformant host cell, and microorganisms and cell cultures transformed with the vector.

As used herein, an IDX-1 variant is a protein sequence that is substantially similar to (i.e., having at least 70% homology and preferably 80–90% homology) the IDX-1 sequence presented in FIG. 1. The sequence of an IDX-1 variant will be sufficiently duplicative of the IDX-1 sequence such that the variant retains the tissue expression pattern of IDX-1 and also retains the ability to transactivate the somatostatin promoter. An IDX-1 variant will include deletion, insertion, or point mutants of IDX-1.

The invention also encompasses IDX-1 variants, including agonists or antagonists of IDX-1, having enhanced or reduced transactivating activity for the somatostatin promoter, and methods for making such variants, comprising: (a) introducing an amino acid alteration into IDX-1 at a site or sites recognized as conferring transactivating activity or binding activity with respect to the somatostatin promoter; and (b) screening the resultant IDX-1 variant for enhanced or reduced transactivating or binding activity in comparison to native IDX-1. Thus, an IDX-1 variant having enhanced binding activity but reduced transactivating activity will include competitive inhibitors of IDX-1, i.e., that competitively inhibit IDX-1 from binding to a given promoter, while providing reduced promoter activation. Alternatively, an IDX-1 variant may have enhanced transactivating activity and enhanced binding activity, and therefore may be considered an agonist of IDX-1. An antagonist or agonist of IDX-1 may contain an insertion, deletion or point mutation of the native IDX-1 sequence.

IDX-1 variants of the invention with enhanced promoter transactivating activity can be used to obtain enhanced expression of a desired gene that is under control of the somatostatin promoter. IDX-1 variants having reduced promoter transactivating activity can be used to obtain reduced expression of a desired gene that is under control of the somatostatin promoter.

Accordingly, the present invention also provides methods for the treatment or prevention of a symptom or condition associated with diabetes comprising administering to a patient having or at risk of developing such symptom or condition a therapeutically effective amount of IDX-1. As used herein, a "therapeutically effective amount" of IDX-1 means the amount of IDX-1 protein that is necessary to restore the level of insulin in the body to a normal level. Symptoms or conditions associated with diabetes include but are not limited to excretion of abnormally high levels of glucose and salts in the urine, frequent urination, and abnormally high levels of glucose in the blood.

IDX-1 as a therapeutic protein can be formulated according to known methods to prepare pharmaceutically useful compositions, whereby the protein is combined in admixture with a pharmaceutically acceptable carrier. Such pharmaceutical compositions are within the scope of the present invention, although the nature of the carrier itself is not an essential aspect of the invention.

The invention features in another aspect, methods of treating diabetes mellitus type I or type II. Thus, according to the invention, the method includes administering to a patient in need thereof a recombinant polypeptide that transactivates sequences found in the somatostatin promoter, the polypeptide being expressed in pancreatic duct cells and not expressed in pancreatic α-cells, the polypeptide being encoded by a gene which encodes a protein on the order of 31 kd, the polypeptide being administered in an amount and for a time sufficient to provide an effective level of endogenous insulin in the patient.

The invention also encompasses methods of treating diabetes mellitus type I or II in which a gene encoding IDX-1, or a variant thereof having enhanced or reduced somatostatin promoter binding activity, is administered in an amount sufficient to promote an effective level of endogenous insulin in the patient.

The invention also encompasses methods of treating diabetes comprising administering to a patient afflicted with diabetes a vehicle carrying a recombinant IDX-1 polypeptide or a variant thereof, or a nucleic acid sequence encoding IDX-1 or a variant, the IDX-1-containing vehicle being administered in an amount sufficient to promote an effective level of endogenous insulin in the patient.

The vehicle may be any carrier of IDX-1 protein that delivers it sufficiently near the site of insulin production in the body such that its administration results in production of an effective level of endogenous insulin. Such vehicles may include, e.g, mammalian cells transfected with a gene encoding IDX-1 or a liposome containing a gene encoding IDX-1.

The invention also encompasses methods of treating diabetes mellitus type I or II in which IDX-1 protein or a variant thereof, or an expressible gene encoding IDX-1, or a variant thereof, is administered to a patient in conjunction with a construct comprising a promoter recognized by IDX-1 or its variant operationally associated with a gene encoding insulin. The gene encoding IDX-1 and the insulin gene construct may be administered to the patient in the same vehicle or in separate vehicles; thus, "in conjunction with" refers to the interactive relationship of the IDX-1 protein on the promoter controlling the insulin gene. Administration may be either simultaneous or sequential administration of the IDX-1 protein or the IDX-1 gene and the expressible insulin gene construct.

Accordingly, as used herein, an "effective" level of endogenous insulin in a patient means the level of insulin produced endogenously in a healthy patient, i.e., a patient who is not afflicted with diabetes mellitus type I or II.

The invention also encompasses a diagnostic kit for detecting a defect in a gene encoding IDX-1, comprising: a nucleic acid probe complementary to the native IDX-1 gene, and means for containing the nucleic acid. Diagnosis of a defect, i.e., a deletion, substitution, or insertion, in the IDX-1 gene may be indicated by failure of the probe to hybridize under stringent conditions to the IDX-1 sequence in a patient's genomic DNA. Such a probe preferably will be at least 50 nucleotides in length, more preferably on the order of 100–200 nucleotides. The diagnostic kit is useful for identifying defects in the IDX-1 gene in order to identify patients who may benefit from exogenous IDX-1 treatment.

In a further aspect, the invention relates to an anti-IDX-1 antibody composition capable of binding to IDX-1. The antibody may be a polyclonal or monoclonal antibody.

In another embodiment, IDX-1 or a variant thereof is used to immunize animals so as to identify antibodies that bind to other domains of IDX-1.

In yet another embodiment, IDX-1 variants are used to screen for other antibodies that bind specifically to the promoter binding domain of IDX-1. In this embodiment, antibodies raised against the native IDX-1 are screened for their ability to bind to an IDX-1 variant of the invention. Antibodies that substantially do not bind to a variant of this invention are selected as being capable of binding to the promoter binding site. Other diagnostic embodiments will be apparent to one of skill in the art.

The invention also features a transgenic mouse whose germ cells and somatic cells contain an inactive IDX-1 gene effective for the promotion of diabetes in the mouse, the inactive gene being introduced into the mouse or an ancestor of the mouse at an embryonic stage.

Further features will become more fully apparent in the following description of the embodiments of this invention and from the appended claims.

BRIEF DESCRIPTION OF THE DRAWINGS

In the drawings:

FIG. 1A shows the sequence of the IDX-1 cDNA and encoded protein.

FIG. 1C is a comparison of the amino acid sequences in the homeodomains of Antp, IDX-1 and selected other homeodomain proteins.

FIGS. 4A–4C show results of immunohistochemistry of IDX-1 or somatostatin (SMS) proteins in RIN1027-B2 cells.

FIGS. 4D–4F show results of immunohistochemistry of IDX-1 or somatostatin (SMS) proteins in rat pancreas cells.

FIGS. 4G–4I show results of immunohistochemistry of IDX-1 or somatostatin (SMS) proteins in rat duodenum cells.

FIG. 6A shows sequence-specific DNA-binding by IDX-1, in which sequences and locations (relative to transcription start site) of DNA elements in the rat somatostatin (SMS) gene 5' flanking region that contain potential IDX-1 binding sites are shown.

FIG. 8 shows translated amino acid sequences of twelve homeodomain cDNAs from rat islet cells, compared with a corresponding homologous region of the Antp homeodomain.

DETAILED DESCRIPTION OF THE INVENTION

Figure 1B:
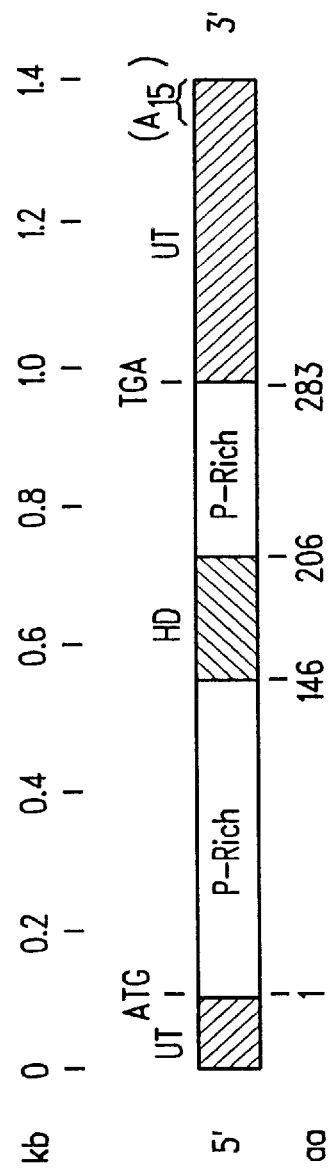
FIG. 1B is a schematic representation of the IDX-1 cDNA and encoded protein.

The invention provides a novel transcription factor, IDX-1, and variants of the factor having the same binding specificity and tissue distribution pattern. The invention also provides in vitro and in vivo uses of IDX-1 and variants thereof. The in vitro uses of IDX-1 are directed to enhanced production of a desired protein encoded by a gene that is under direction of an IDX-1-sensitive promoter; examples of such promoters include but are not limited to the somatostatin promoter (Taviani et al., 1984, Jour. Biol. Chem. 259:11798), hereby incorporated by reference, the insulin promoter (Karlsson et al., 1987, Proc. Nat. Aca. Sci. USA 84:8819), hereby incorporated by reference, and the glucagon promoter (Phillippe et al., 1988, Mol. and Cell. Biol. 8:4877), hereby incorporated by reference. The diabetes treatment methods are aimed at manipulation of the developmental transition from non-islet pancreatic cells to pancreatic islet cells and from pancreatic α-cells to pancreatic β-cells by providing IDX-1 ex vivo or in vivo. Thus, the methods may relate to manipulation of three cell types. First, treatment of type I diabetes may be accomplished according to ex vivo methods, e.g., by promoting the replenishment of β-cells from non-β-pancreatic cells. Alternatively, type I diabetes may be treated by stimulating maturation of pancreatic β-cells from progenitor cells such as pancreatic ductal cells using IDX-1. Type II diabetes may be treated according to the invention by boosting the production of insulin directly using IDX-1 or by increasing pancreatic islet cell mass. The DNA and amino acid sequences of the novel IDX-1 transcription factor are described below, along with the in vitro and in vivo uses therefore.

The following examples provide guidance to one of ordinary skill in the art on how to make and use the invention. These examples are not meant to limit the invention, but provide an enabling basis therefore.

EXAMPLE I

The novel recombinant polypeptide of the invention may be made using information provided herein as to its nucleotide and amino acid sequences, using conventional recombinant DNA and protein production techniques. See Maniatis et al., supra. The novel recombinant polypeptide may be obtained by first cloning the gene encoding the polypeptide, as described herein, using a probe at least 50 nucleotides in length corresponding to a portion of the nucleotide sequence shown in FIG. 1: e.g., the 5' and/or 3' 50 nucleotides of the coding region, or any 50 nucleotide sequence therebetween.

Isolation and Characterization of a Novel Transcription Factor

IDX-1 is a newly discovered homeodomain transcription factor isolated from a somatostatin-producing, rat islet-derived cell line, RIN1027-B2. The results presented herein demonstrate that IDX-1 is expressed in pancreatic islets and ducts, and in the duodenum, and binds to and activates transcription from regulatory sequence elements in the 5' flanking region of the rat somatostatin gene. IDX-1 appears to be the first homeodomain protein identified thus far to regulate somatostatin gene transcription. IDX-1 contains an Antp-type homeodomain flanked by proline rich regions in both the amino and carboxyl domains of the protein. The homeodomain of IDX-1 is presumably involved in sequence-specific DNA binding, whereas, as has been determined for the transcription factor CTF/NF-1 (Mermod et al., 1989, Cell 58:741), the proline rich regions in IDX-1 may function in transcriptional activation.

During embryonic development in rodents, the primordial pancreatic anlaga are formed from outpocketings of the primitive gut on or around gestation day 10 (Pictet and Rutter, 1972, Handbook of Physiology 1:25). Cells within the pancreatic anlaga subsequently differentiate and give rise to exocrine and endocrine tissues. The initial formation of the pancreatic anlaga coincides with the first appearance of digestive enzymes of the exocrine pancreas and the hormones produced by the endocrine pancreas (Pictet and Rutter, 1972, Handbook of Physiology 1:25). In the early stages of pancreatic development in rodents, the endocrine cells are found in close proximity to the pancreatic ducts, and are believed to be derived from stem cell populations in or around the ducts (Alpert et al., 1988, Cell 53:295; Dudek et al., 1991, Diabetes 40:1041; Yoshinari and Diakoku, 1982, Anat. Embryol. 165: 63). During pancreatic islet development there is an ordered progression in the appearance of the major islet hormones. Glucagon-producing α cells are first detected on gestation day 10, whereas insulin-producing β cells and somatostatin-producing δ cells first appear on gestation days 12 and 17, respectively (Pictet and Rutter, 1972, supra). Cellular phenotypes are established by selective transcriptional activation or repression of cell-specific sites of genes, which are accomplished by the interaction of DNA binding proteins with their corresponding DNA regulatory elements and with the proteins of the general transcription machinery. Homeodomain transcription factors are sequence-specific DNA binding proteins known to be important in directing embryonic development and determining differentiated cell identity in a wide variety of organisms (Gehring, 1987, Science 236:1245; Holland and Hogan, 1988, Genes & Dev. 2:773; Blumberg et al., 1991, Science 253:194; Nohno et al., 1991, Cell 64:1197; Levine and Schechter, 1993, Proc. Natl. Acad. Sci. USA 90:2729; Bellmann and Werr, 1992, Embo J. 11:3367; Schummer et al., 1992, Embo J. 11:1815; Burglin et al., 1989, Nature 341:239). The homeodomain is a highly-conserved 61-amino acid DNA-binding structure first identified in homeotic selector genes of drosophila melanogaster (Gehring, 1987, supra; Scott et al., 1989, Biochem. Biophys. Acta. 989:25). As part of an effort to identify and characterize DNA-binding proteins involved in pancreatic islet development and differentiation, homeodomain-encoding cDNAs were cloned from a λgt11 cDNA library prepared from the somatostatin-producing islet cell line RIN1027-B2 (Philippe et al., 1987, J. Clin. Invest. 79:351).

The homeodomain consists of three a-helical regions separated by a loop and a turn. The high degree of conservation of amino acid sequences within portions of the first and third helices (Scott et al., 1989, supra) has facilitated the cloning of homeodomain cDNAs (Burglin et al., 1989, supra; Singh et al., 1991, Proc. Natl. Acad. Sci. USA 88:10706; Patel et al., 1992, J. Biol. Chem. 267:26085; James and Kazenwadel, 1991, J. Biol. Chem. 266: 3246; Murtha et al., 1991, Proc. Natl. Acad. Sci. USA 88:10711; Nazarali et al., 1992, Proc. Natl. Acad. Sci. USA 89:2883; Levine and Schechter, 1993, supra). The most highly conserved region of the homeodomain is the amino acid sequence KIWFQN within the DNA recognition helix (helix three). Thus, a degenerate oligonucleotide corresponding to this sequence was used (Burglin et al., 1989, supra) to screen the RIN1027-B2 cDNA library for homeodomain-containing cDNAs. A second highly conserved amino acid sequence, ELEKEF, within the first helix of the homeodomain was utilized to design a degenerate polymerase chain reaction (PCR) amplimer (James and Kazenwadel, 1991, supra). This was used, in conjunction with a degenerate PCR amplimer corresponding to the KIWFQN motif in the third helix, to amplify homeodomain-containing cDNAs from rat islet cDNA. By using this confined approach, a complete cDNA was isolated for IDX-1 (Islet/Duodenum Homeobox-1), a novel homeodomain protein from the RIN1027-B2 cDNA library, and homeodomain proteins expressed in rat islets were surveyed. Experiments presented herein describe the cloning of IDX-1, its cell- and tissue-specific expression in pancreatic islets and ducts, and duodenum, and its DNA binding and transcriptional regulatory activities. Furthermore, it is shown herein that IDX-1 appears to be the most abundant homeodomain mRNA in rat islets. Eleven additional homeodomain mRNAs expressed in rat islets are identified.

The following examples delineate in detail the cloning and characterization of the novel transcription factor, IDX-1. These examples are presented to illustrate advantages of the invention and to assist one of ordinary skill in making and using the same; for example, in the cloning and characterization of other novel transcription factors. The examples are not intended to limit the scope of the invention.

1. Isolation and sequence analysis of the IDX-1 cDNA.

A λgt11 cDNA library from RIN1027-B2 cells was screened at low stringency with a $^{32}$P-labelled single-stranded degenerate oligonucleotide (HB-1) corresponding to the most highly conserved amino acid residues (KIWFQN) in helix three of the Antennapedia (Antp) homeodomain (Burglin et al., 1989, supra). cDNA inserts from plaque purified phage were amplified by polymerase chain reaction (PCR), subcloned into pBluescript(KS) (Stratagene, Torrey Pines Calif.), and sequenced by the dideoxy chain termination method (Sequenase, USB, Cleveland Ohio) using T3 and T7 primers. Initial screening with $^{32}$P-labelled HB-1 yielded 18 plaque purified recombinant phage. Two of these contained identical 0.8 kb cDNA inserts with high sequence similarity to XLHbox8, an endoderm-specific homeobox transcription factor expressed in the pancreatic anlagen of xenopus laevis (Wright et al., 1988, Development 104: 787). These cDNA inserts correspond to partial IDX-1 clones. One of these cDNAs was labelled with 32p and used to rescreen the RIN1027-B2 cDNA library to isolate a 1.4 kb IDX-1 cDNA.

FIG. 1A shows the sequence of the IDX-1 cDNA and encoded protein. The IDX-1 cDNA contains an open reading frame encoding the 283 amino acid protein, 150 nucleotides of 5' untranslated and 500 nucleotides of 3' untranslated sequence. The IDX-1 protein has an estimated molecular weight of 31 kDa, contains a homeodomain (underlined in FIG. 1A), and has proline-rich regions in its amino and carboxy terminal regions (FIG. 1A and 1B). FIG. 1B is a schematic representation of the IDX-1 cDNA and encoded protein. Translation start (ATG) and stop (TGA) codons are indicated. HD means homeodomain region; P-Rich means proline-rich region; and UT means untranslated region. As expected, the IDX-1 homeodomain is similar to Antp, particularly in the first and third helices (FIG. 1C). FIG. 1C is a comparison of the amino acid sequences in the homeodomains of Antp, IDX-1 and selected other homeodomain proteins. Numbers above the Antp sequence indicate amino acid position within the homeodomain. Dashes denote sequence identity with Antp. Note that the only available sequence for XLHbox8 is from a partial clone beginning at amino acid residue 19 in the homeodomain (Wright et al., 1988, supra). These regions are the most highly conserved among the vast majority of known homeoproteins (Scott et al., 1989, supra).

Immediately below IDX-1 in FIG. 1C is the amino acid sequence for a portion of the homeodomain of XLHbox8, a homeobox protein expressed in the developing and mature duodenum and pancreas of xenopus laevis. The only published sequence for XLHbox8 is from a partial clone beginning at amino acid residue 19 in the homeodomain (Wright et al., 1988, supra). There is no available XLHbox8 sequence 5' to this site. The amino acid sequence of IDX-1 is identical to that of XLHbox8 from residues 19 to 60 of the homeodomain, while the sequences of the two proteins diverge completely just carboxy proximal to the homeodomain. There is 80% nucleic acid similarity between IDX-1 and XLHbox8 within the homeodomain. The high degree of sequence similarity in the IDX-1 and XLHbox8 homeodomains and similar patterns of expression suggests that the two proteins may be closely related, or that IDX-1 is the rat homologue of XLHbox8.

2. Tissue distribution of IDX-1.

The tissue distribution of IDX-1 mRNA was determined using Northern blot analysis. Total RNA prepared from rat tissues or cell lines (Ausubel et al., 1992, Short Protocols in Molecular Biology, Second Edition) was fractionated on formaldehyde/1% agarose gels, then transferred to nylon membranes (MSI, Westborough, Mass.). RNA bound to the membranes was hybridized overnight at 48° C. with random primed $^{32}$P-labelled cDNA probes for rat IDX-1 or chicken β-actin (Cleveland et al., 1980, Cell 20:95). Membranes were washed and dried, then analyzed by autoradiography.

Figure 2A:
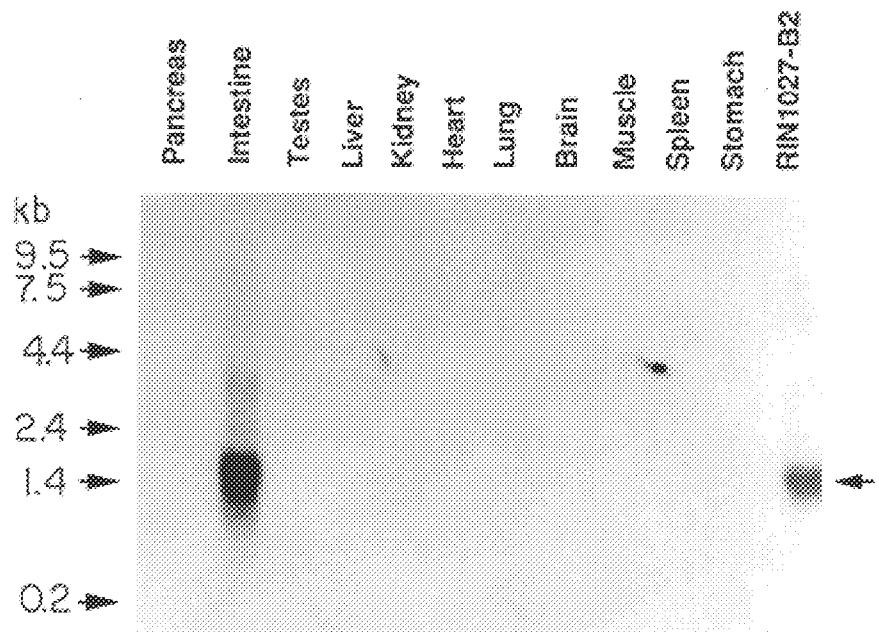
FIG. 2A shows results of Northern analysis of IDX-1 mRNA in adult rat tissues, particularly intestine.
Figure 2B:
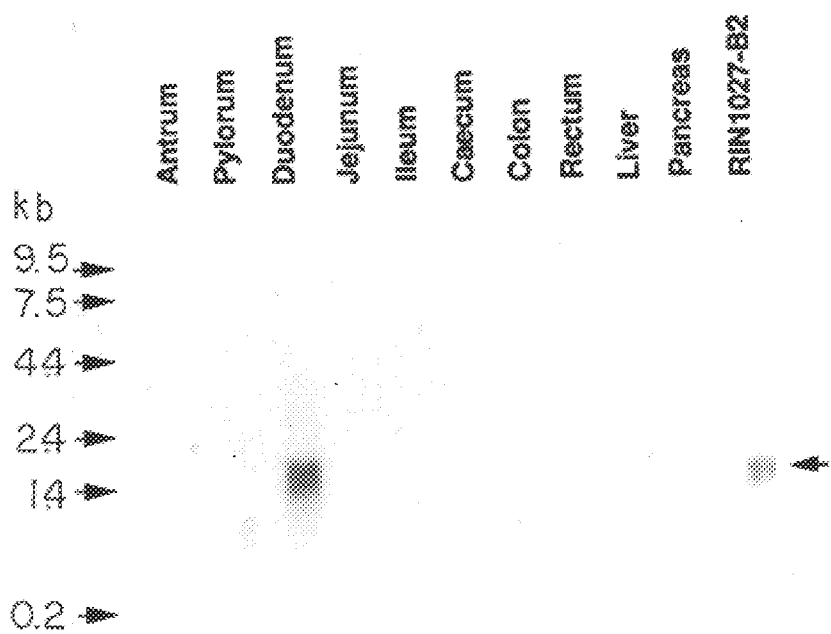
FIG. 2B shows results of Northern analysis of IDX-1 mRNA in adult rat tissues, particularly duodenum.
Figure 2C:
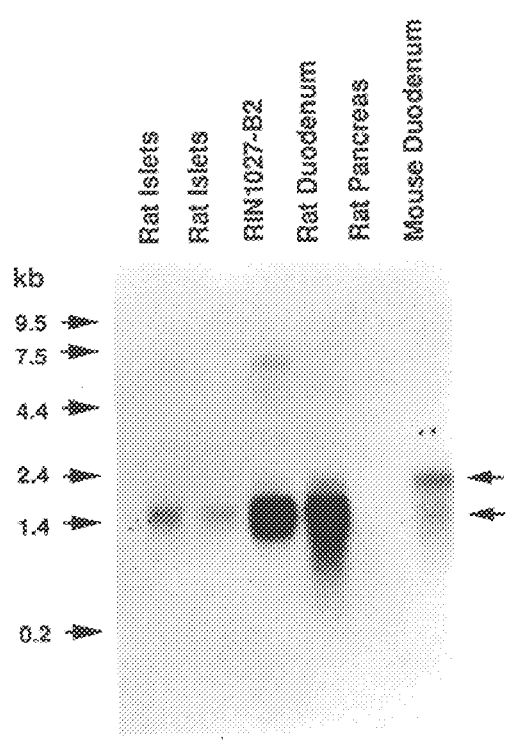
FIG. 2C shows results of Northern analysis of IDX-1 mRNA in adult rat tissues, particularly islets.

Northern analysis of total RNA from adult rat tissues indicates that the 1.5 kb IDX-1 mRNA is expressed in pancreatic islets and duodenum. FIGS. 2A–C shows results of Northern analysis of IDX-1 mRNA in adult rat tissues. Twenty μg of total RNA from each tissue or 10 μg of total cellular RNA from RIN1027-B2 cells were loaded per lane. Initially, a multiple tissue Northern blot showed that IDX-1 mRNA was detected only in intestine (FIG. 2A). This observation prompted us to examine other segments of the rat gastrointestinal tract for IDX-1 expression. As shown in FIG. 2B, IDX-1 mRNA can be detected in the duodenum, but not in any other section of the gastrointestinal tract. IDX-1 mRNA is detected at uniform levels along the first 8 cm of the rat duodenum (data not shown). Since IDX-1 was cloned from a rat pancreatic islet-derived cell line, it was of interest to determine whether IDX-1 mRNA is expressed in rat islets. Northern analysis indicates that the IDX-1 mRNA is detected in rat islet RNA (FIG. 2C). Also shown in FIG. 2C is a weakly hybridizing band from mouse duodenum RNA that is approximately 2.0 kb. Lack of detectable IDX-1 mRNA in RNA preparations from whole pancreas and that some islet-specific mRNAs are diluted out to undetectable levels by the non-islet contribution to total pancreatic RNA.

Figure 2D:
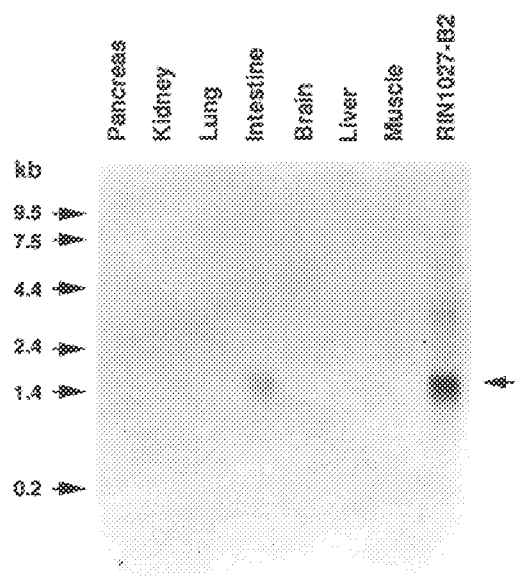
FIG. 2D shows results of Northern analysis of IDX-1 mRNA in fetal rat tissues (gestation day 20).

FIG. 2D shows results of Northern analysis of IDX-1 mRNA in fetal rat tissues (gestation day 20). IDX-1 mRNA is also detected in RNA prepared from fetal rat whole intestine at gestation day 20. During embryonic development, the pancreas is derived from the duodenum. The observation that IDX-1 mRNA is detected in adult rat islets and duodenum, and in fetal intestine, suggests a role for IDX-1 in pancreatic development.

The presence of IDX-1 protein in tissues was determined using Western blot analysis and antiserum to IDX-1. Antiserum to IDX-1 was raised in rabbits immunized (Hazelton Research Products, Denver, Pa.) with a bacterially-expressed recombinant glutathione S-transferase/IDX-1 fusion protein (Smith and Johnson, 1988, Gene 67:31) containing amino acid residues 164-283 of rat IDX-1. The R1090 CREB antiserum has been described (Lee et al., 1990, Euro. Jour. Mol. Biol. 9:4455). Crude nuclear lysates were prepared from rat duodenum and jejunum by isolating nuclei from these tissues through a sucrose cushion (Gorski et al., 1986, Cell 47:767), then lysing the nuclei in SDS sample buffer (Laemmli, 1970, Nature 277: 680). Pancreatic islet whole cell lysates were prepared by lysing freshly isolated rat islets in SDS sample buffer. Whole cell lysates from RIN1027-B2 cells were prepared in a similar manner. Lysates were sonicated then cleared by centrifugation (10, 000×G, 4° C.). Nuclear extracts were prepared from cultured cells by the method of Dignam et al. (1983, Nucleic Acids Res. 11: 1475). Extracts and lysates were fractionated on SDS-polyacrylamide gels and electroblotted onto nitrocellulose membranes (MSI). The membranes were incubated with primary antisera (1:20,000), and subsequently with an alkaline phosphatase-conjugated goat anti-rabbit secondary antibody (BioRad Laboratories, Richmond Calif.). Immunoreactive proteins were visualized using the ECL chemiluminescent detection system (Amersham Inc., Arlington Heights, Ill.).

Figure 2E:
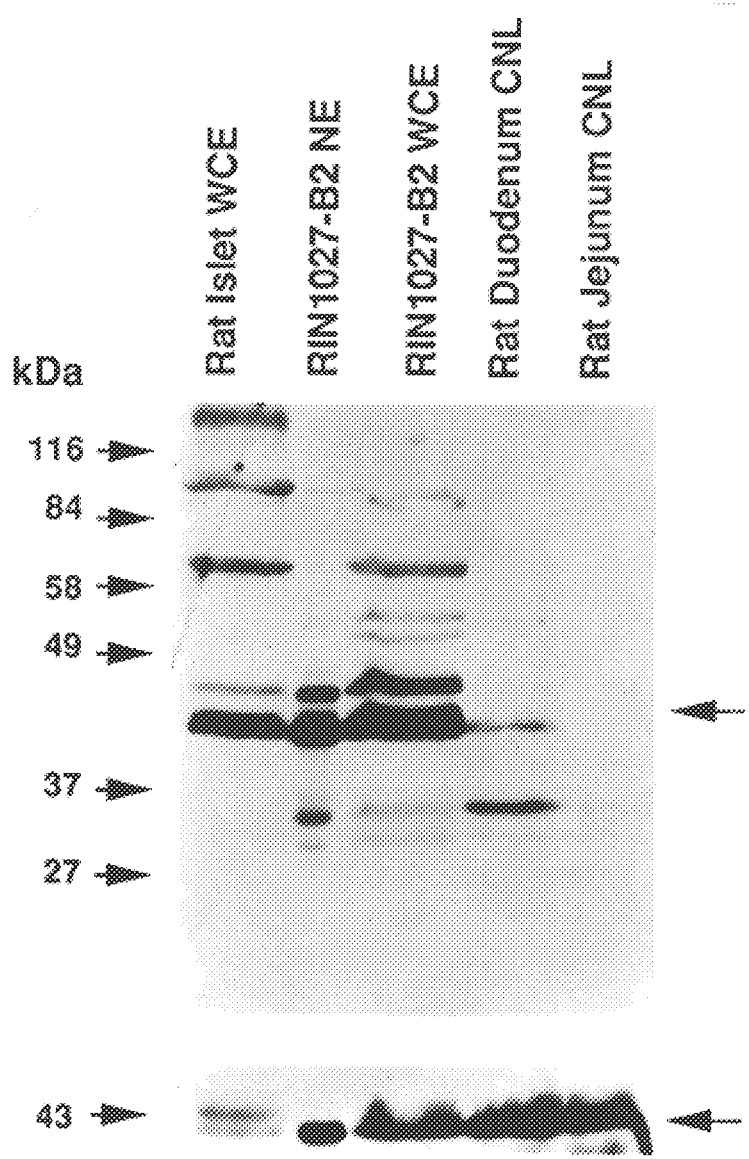
FIG. 2E shows results of Western immunoblot analysis of IDX-1 (top) and CREB (bottom) proteins in adult rat tissues (NE, Nuclear Extracts; WCE, Whole Cell Extracts, CNL, Crude Nuclear Lysates).

Western immunoblot analysis of rat tissue extracts indicate that, as for IDX-1 mRNA, IDX-1 protein is detected in rat islets and duodenum. The major protein displaying IDX-1 immunoreactivity in Western immunoblot analysis of rat islet whole cell extracts, RIN1027-B2 nuclear and whole cell extracts, and crude nuclear lysates from duodenum migrates with an apparent molecular weight of 42 kDa. FIG. 2E shows results of Western immunoblot analysis of IDX-1 (top) and CREB (bottom) proteins in adult rat tissues (NE, Nuclear Extracts; WCE, Whole Cell Extracts; CNL, Crude Nuclear Lysates). COS-1 cells transfected with an IDX-1 eukaryotic expression vector also produce IDX-1 protein with an apparent molecular weight of 42 kDa. In addition, the major bands of IDX-1 immunoreactivity and radioactivity form IDX-1 transcribed and translated in vitro, or immunoprecipitated from $^{35}$S-labelled RIN1027-B2 cells are also 42 kDa (data not shown). The CREB protein is easily detected in all of these extracts and lysates indicating that lack of IDX-1 protein in jejunum was not due to sample degradation or variable loading.

3. Expression of IDX-1 in cultured cell lines.

Figure 3A:
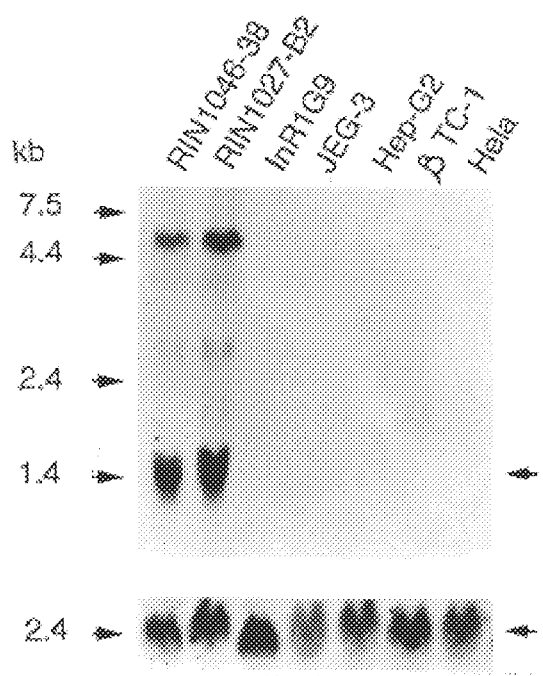
FIG. 3A is a Northern analysis of IDX-1 (top) and actin (bottom) mRNAs in assorted cultured cell lines.
Figure 3B:
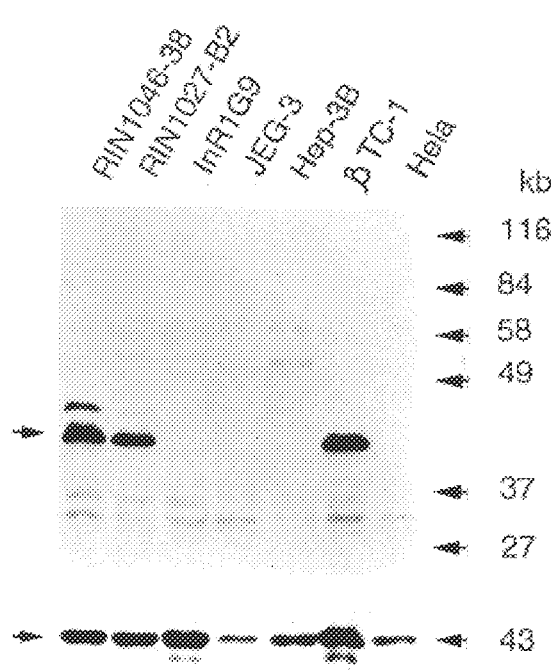
FIG. 3B is a Western immunoblot analysis of IDX-1 (top) and CREB (bottom) proteins in nuclear extracts prepared from assorted cultured cell lines.
Figure 5A:
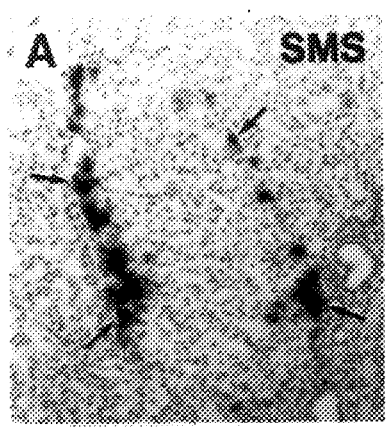
FIGS. 5A–5C show results of in situ hybridization of somatostatin (SMS) or IDX-1 in rat pancreas cells (5A–5C, X1480).
Figure 5B:
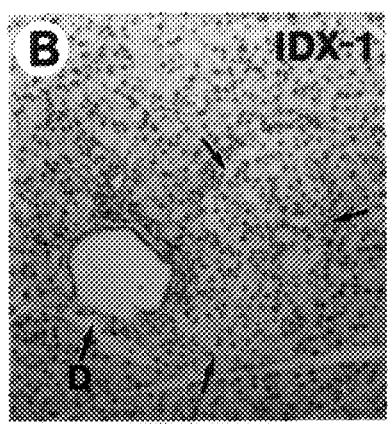
Figure 5C:
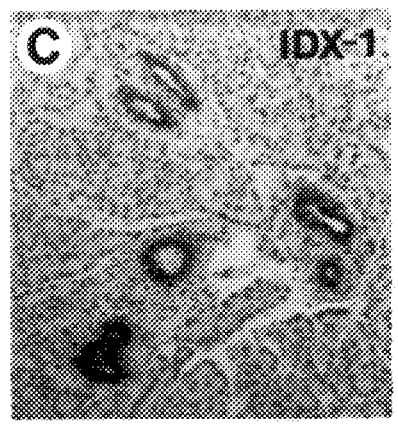
Figure 5D:
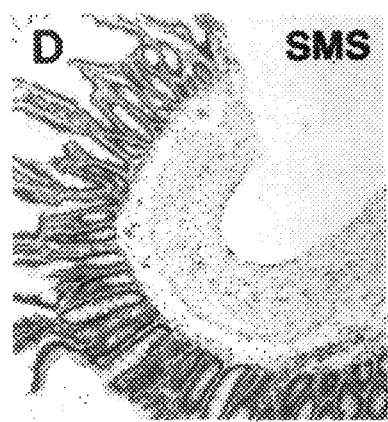
FIGS. 5D–5F show results of in situ hybridization of somatostatin (SMS) or IDX-1 in rat duodenum cells; 5D, pancreatic duct (5D–5E, X740; 5F, X1480).
Figure 5E:
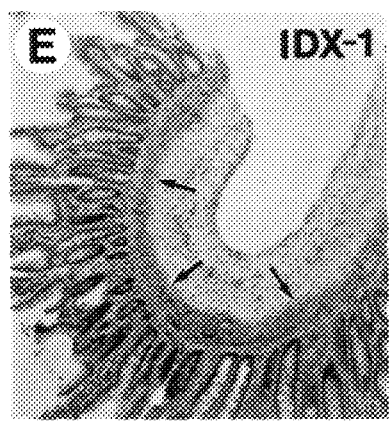
Figure 5F:
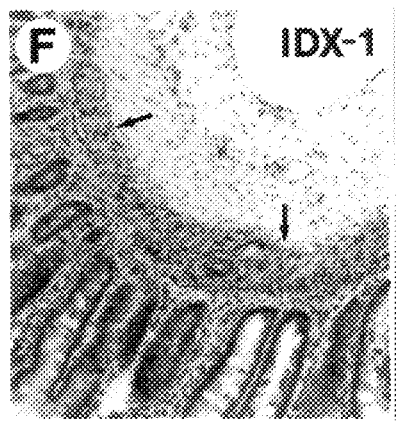

Several islet and non-islet cell lines were assayed for IDX-1 expression by Northern RNA blot and Western immunoblot (FIGS. 3A and 3B). RIN1046-38 and RIN1027-B2 cells are derived from a radiation-induced rat insulinoma (Chick et al., 1977, Proc. Natl. Acad. Sci. USA 74:628; Philippe et al., 1987, supra). RIN1046-38 cells produce insulin and most closely resemble islet β-cells, whereas RIN1027-B2 cells produce somatostatin and have more features of islet δ-cells. InRlG9 cells are a glucagon-secreting hamster islet cell line (Takaki et al., 1986, In Vitro Cell. & Dev. Biol. 22:120), and have characteristics of islet α-cells. βTC1 cells are a mouse islet β-cell line (Efrat et al., 1988, Proc. Natl. Acad. Sci USA 85:9037). JEG-3, HepG2 and Hela cells are derived from non-islet tissues.

RIN1027-B2, RIN1046-38 (Chick et al., 1977, supra; Philippe et al., 1987, supra), InR1G9 (Takaki et al., 1986, supra), HepG2, Hep3B, JEG-3, and Hela cells (ATCC HB8065, HB8064, HTB36, and CCL2, respectively) were cultured at 37° C. in Dulbecco's Modified Eagle's Medium supplemented with 10% fetal bovine serum, 100 units of penicillin per ml, and 100 μg of streptomycin per ml. NIH-3T3 cells (ATCC CRL1658) were cultured in DMEM with the same antibiotics and 10% calf serum. βTC1 cells (Efrat et al., 1988, supra) were cultured in RPMl-1640 with 10% fetal bovine serum and antibiotics. All cell culture reagents were obtained from GIBCO (Grand Island, N.Y.).

The results showed that IDX-1 is expressed in several islet-derived cell lines but is not detected in non-islet cell lines. FIG. 3A is a Northern analysis of IDX-1 (top) and actin (bottom) mRNAs in assorted cultured cell lines. Fifteen μg of total cellular RNA were loaded per lane. FIG. 3B is a Western immunoblot analysis of IDX-1 (top) and CREB (bottom) proteins in nuclear extracts prepared from assorted cultured cell lines. IDX-1 mRNA (FIG. 3A) and protein (FIG. 3B) are present only in islet-derived cell lines, and are expressed in β- and δ-, but not in α-cell lines.

4. Immunohistochemistry and in situ hybridization.

Western immunoblot analysis indicated that IDX-1 protein was present in rat islets and duodenum (FIG. 2E). Immunohistochemistry was performed with RIN1027-B2 cells and rat islets and duodenum to gain further information regarding the tissue and cellular localization of IDX-1 protein. RIN1027-B2 cells grown on chamber slides (Falcon, Oxnard, Calif.), or freshly cut frozen pancreas and duodenum sections were fixed with 4% paraformaldehyde in phosphate-buffered saline, permeabilized in acetone at −20° C., and incubated overnight at 4° C. with IDX-1 antiserum. To visualize IDX-1 protein, slides were incubated with a biotinylates secondary antibody, and then an avidin-biotinylated horseradish peroxidase complex (Vectastain ABC System, Vector Laboratories, Burlingame, Calif.).

FIG. 4 shows results of immunohistochemistry of IDX-1 or somatostatin (SMS) proteins in RIN1027-B2 cells (panels A–C), rat pancreas (D–F) and rat duodenum (G–I). Panels A, D, and E correspond to preimmune serum; Panels B, E, H, and I to IDX-1 antiserum; and Panels C and F to somatostatin antiserum. (A–C, and I, X1480; D and E, X740).

The results of the immunohistochemistry assays using antiserum to IDX-1 clearly shows the presence IDX-1 in the nuclei of RIN1027-B2 cells (FIG. 4, panel B). This immunostaining is absent in cells incubated with preimmune serum (FIG. 4, panel A).

Nuclear localization for IDX-1 is consistent with a proposed role as a transcriptional regulator, and with the detection of IDX-1 protein in RIN1027-B2 nuclear extracts by Western immunoblot analysis (FIGS. 2E and 3B). High levels of somatostatin immunoreactivity are present in only 10–20% of the RIN1027-B2 cells (FIG. 4, panel C), suggesting that although IDX-1 may regulate somatostatin gene transcription (FIG. 7), its presence is not the sole determinant for somatostatin gene expression. Immunostaining of rat pancreas sections with IDX-1 antiserum indicates that IDX-1 protein is present in islets but not in the exocrine pancreas (FIG. 4, panel E). The presence of immunopositive cells in the islet core and periphery suggests that IDX-1 may be found in multiple islet cell phenotypes. In rodents, the islet core contains mainly insulin-producing β-cells, whereas the islet periphery is predominantly composed of somatostatin-producing δ-cells and glucagon-producing α-cells (Orci, 1982, Diabetes 31:538). Within the duodenum, IDX-1 immunopositive nuclei are visible in cells of the intestinal crypts (FIG. 4H and I).

In situ hybridization was performed to examine tissue and cellular localization of IDX-1 mRNA in rat pancreas and duodenum sections (FIG. 5). Rat pancreas and duodenum samples were excised and fixed overnight at 4° C. with 4% paraformaldehyde in phosphate-buffered saline. Tissue samples were dehydrated and embedded in paraffin. Sections were cut and in situ hybridization performed with $^{35}S$-labelled cDNA or cRNA probes for rat somatostatin or IDX-1 mRNA (Simmons et al., 1989, J. Histotechnology 12:169).

FIG. 5 shows results of in situ hybridization of somatostatin (SMS, panels A and D) or IDX-1 (panels B, C, E, and F) mRNAs in rat pancreas (A–C) and duodenum (D–F) (D, pancreatic duct; A–C and F, X1480, and D and E, X740). In the pancreas, IDX-1 mRNA is most easily detected in pancreatic ducts and in mesenchymal cells surrounding the ducts (FIG. 5C, and "D" in FIG. 5B). Pancreatic islets are only weakly positive for IDX-1 mRNA (FIG. 5B). Within the duodenum, IDX-1 mRNA is localized to a broad band within the submucosal region (FIG. 5E), and to a lesser extent, in cells at the base of the crypts (FIG. 5F).

5. Sequence-specific DNA binding by IDX-1.

Electrophoretic mobility shift assays (EMSA) were used to characterize the DNA binding properties of IDX-1. EMSA/PCR-based selection and amplification of DNA binding sites (Sun and Baltimore, 1991, Cell 64:459) indicated that bacterially-expressed IDX-1 preferentially binds to the sequence 5'-TAAT(T/G)-3' (not shown). The preference for this motif is shared by other homeoproteins (Desplan et al., 1988, Cell 54:1081; Scott et al., 1989, supra; Ekker et al., 1991, Embo J. 10:1179). Since the IDX-1 cDNA was isolated from a rat somatostatin-producing islet derived cell line (RIN1027-B2), we examined the rat somatostatin gene 5' flanking region for potential binding sites. The 5'-TAAT(T/G)-3' motif occurs three times within five hundred nucleotides upstream of the transcription start site in the rat somatostatin gene.

Electrophoretic mobility shift assays (EMSA) were performed as described (Ron et al., 1990, Mol. and Cell. Biol. 10:1023) using bacterially-expressed IDX-1 or nuclear extracts prepared from RIN1027-B2 cells (Dignam et al., 1983, supra). PCR was used to generate a bacterial expression vector encoding the full length IDX-1 protein fused to glutathione S-transferase(GST). An oligonucleotide amplimer was designed to create an NcoI site at the initiation methionine of the IDX-1 cDNA. This primer was used in conjunction with the T3 primer to amplify the IDX-1 cDNA insert from an IDX-1/pBS(KS) subclone. The PCR product was digested with NcoI and XhoI, gel-purified, and ligated into NcoI/XhoI-cut pGEX-KG (Pharmacia Biotech Inc., Piscataway, N.J.). Expression and purification of the GST/IDX-1 fusion protein was performed as described (Smith and Johnson, 1988, supra).

Nuclear extracts form RIN1027-B2 cells or purified bacterially-expressed GST/IDX-1 were incubated with the following $^{32}P$-labelled double-stranded oligonucleotide probes: 1) INS1-FLAT, the Far-linked AT-rich element of the rat insulin 1 gene (German et al., 1992, Mol. Cell. Biol. 12:1777) (5'-GATCCTTGTTAATCTAATT ACCCTAGGTCTAA-3'); 2) SMS-TAAT1, a FLAT-like element (5'-GATCCCTGATTGCATATTAATTC TCAGA TA-3') located at nucleotides −438 to −461, relative to the transcription start site, of the rat somatostatin gene; 3) SMS-TAAT2, a second FLAT-like element in the rat somatostatin gene (nucleotides −290 to −303; 5'-GATCCGAT CTCAGTAATTAATCATGCACCA-3'); 4) SMS-UE-B, the B domain of the rat somatostatin upstream enhancer element (Vallejo et al., 1992a, 1992b, J. Biol. Chem. 267:12868, 12876) (nucleotides -83 to -106; -5'-GATCCGCGAGGCTAATGGTGCGTAAAAGCACTGG-TGA-3'); 5) SMS-PS, a transcriptional silencer element in the rat somatostatin gene (Vallejo et al., in preparation; nucleotides −219 to −233: 5'-GATCCAGGCAAGATTATTTGGTCA-3'). These oligonucleotides all contain 5'-TAAT-3' motifs that are typical of DNA sites recognized by homeodomain transcription factors (Scott et al., 1989, supra; Desplan et al., 1988, supra; Ekker et al., 1991, supra). After incubation with the probes, DNA-protein complexes were resolved on non-denaturing polyacrylamide gels, then visualized by autoradiography of the dried gels.

Figure 6B:
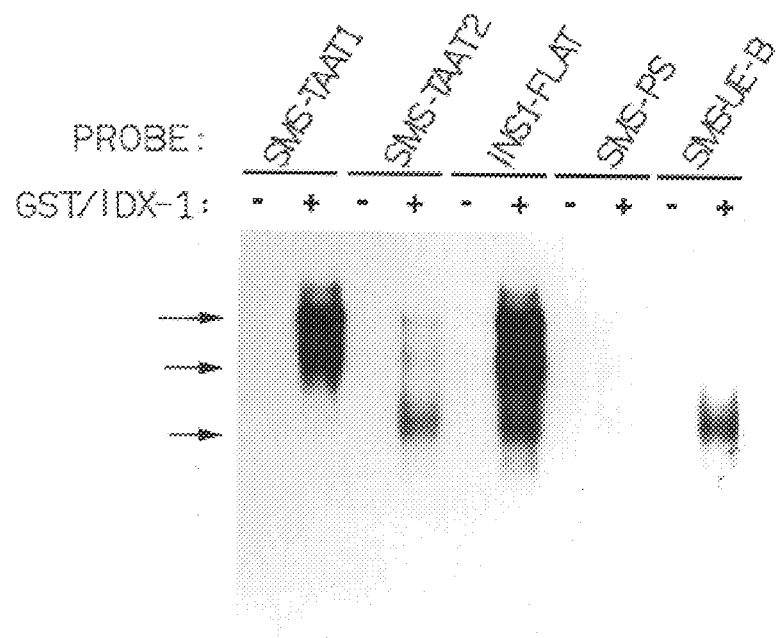
FIG. 6B shows results of an electrophoretic mobility shift assay (EMSA) with bacterially-expressed IDX-1 and $^{32}$P-labelled oligonucleotide probes corresponding to the sequences shown in FIG. 5(A).
Figure 6C:
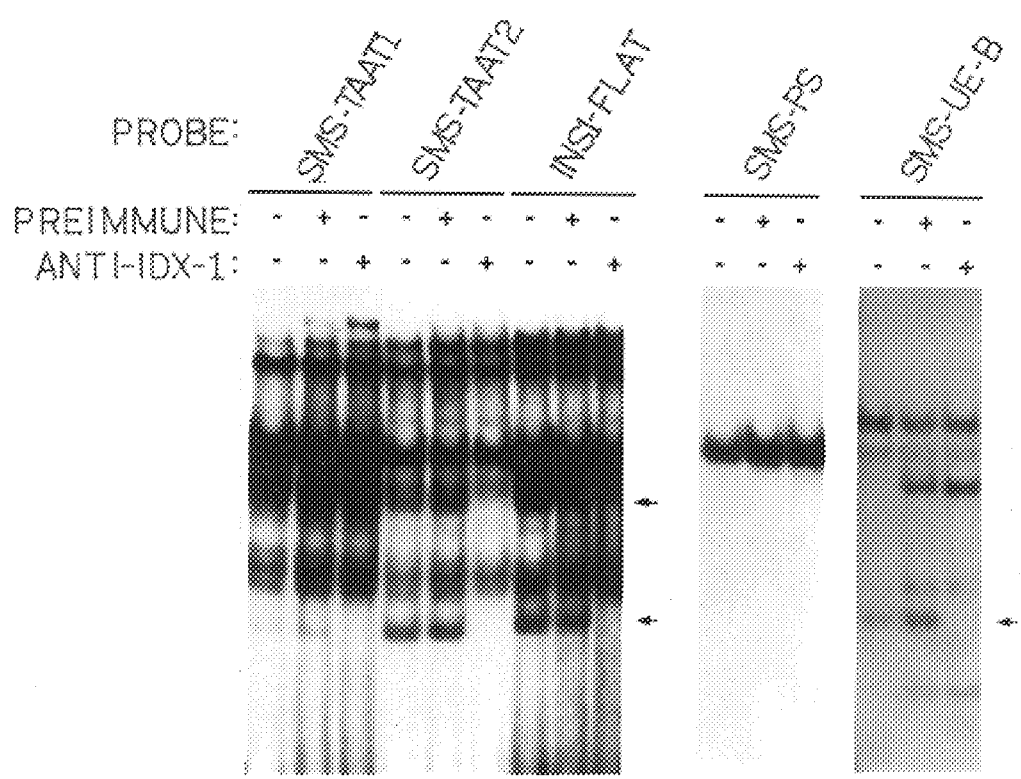
FIG. 6C shows EMSA with RIN1027-B2 nuclear extracts and the oligonucleotide probes shown in FIG. 5A.

FIG. 6 shows sequence-specific DNA-binding by IDX-1. In FIG. 6A, sequences and locations (relative to transcription start site) of DNA elements in the rat somatostatin (SMS) gene 5' flanking region that contain potential IDX-1 binding sites are shown. Also shown is the sequence of the Far-Linked AT-Rich element, (INS1-FLAT) a homeodomain binding sequence in the rat insulin 1 gene minienhancer (German et al., 1992, supra), and also a potential IDX-1 binding site. The 5'-TAAT-3' motifs are underlined. In FIG. 6B, results of an electrophoretic mobility shift assay (EMSA) is shown with bacterially-expressed IDX-1 and $^{32}P$-labelled oligonucleotide probes corresponding to the sequences shown in FIG. 5(A). FIG. 6C shows EMSA with RIN1027-B2 nuclear extracts and the oligonucleotide probes shown in FIG. 5A. DNA/protein binding reactions were performed either under standard conditions, or with the addition of preimmune serum or IDX-1 antiserum. Arrows indicate the DNA/protein complexes that are selectively disrupted by IDX-1 antiserum.

The sequences shown in FIG. 6A are compared with the FLAT element of the rat insulin 1 gene (INS1-FLAT), a target site for several homeodomain proteins in insulin-producing cells (German et al., 1992, supra; Emens and Moss, 1992, Proc. Natl. Acad. Sci. USA 89:7300), that also contains a potential IDX-1 binding site. The SMS-TAAT1 and SMS-TAAT2 sequences are two elements in the rat somatostatin gen 5' flanking region that bear strong similarity to the INS1-FLAT site. The SMS-UE-B sequence corresponds to the B-domain of the somatostatin upstream element, a bipartite cell-specific enhancer that functions synergetically with a nearby cAMP response element (Vallejo et al., 1992a, and 1992b, supra). The SMS-PS (Proximal Silencer; Vallejo et al., in preparation) probe contains a 5'-TAATC-3' sequence (non-coding strand) and was included for comparison as an element that did not contain the preferred IDX-1 target sequence. In EMSA with $^{32}$P-labelled probes corresponding to these sequences, bacterially-expressed IDX-1 binds to the probes containing the 5'-TAAT(T/.G)-3' motif, but does not bind to the 5'-TAATC-3' SMS-PS probe (FIG. 6B). The SMS-TAAT1 and INS1-FLAT probes form several complexes with IDX-1, which may correspond to single or multiple molecules of IDX-1 binding to the probes.

EMSA with RIN1027-B2 nuclear extracts were conducted using the same probes shown in FIG. 6A and 6B. Binding reactions were performed with or without the addition of IDX-1 antiserum or preimmune serum. Comparison of the EMSA patterns and results from cross-competition experiments (not shown) indicate that several DNA-protein complexes are shared among these probes. One of the fastest migrating complexes for the SMS-TAAT1, SMS-TAAT2, INS1-FLAT, and SMS-EU-B probes is disrupted by the addition of IDX-1 antiserum (FIG. 6C), indicating IDX-1 binding to these sites. Addition of preimmune serum does not alter the EMSA pattern. A second band of slower mobility with the SMS-TAAT2 and INS1-FLAT probes is also disrupted by IDX-1 antiserum. The faster migrating band is not seen for the SMS-PS probe, and no bands are perturbed by the IDX-1 antiserum, consistent with the lack of SMS-PS binding by bacterially-expressed IDX-1 (FIG. 6B).

EXAMPLE II

Transcriptional activation by IDX-1.

Figure 7A:
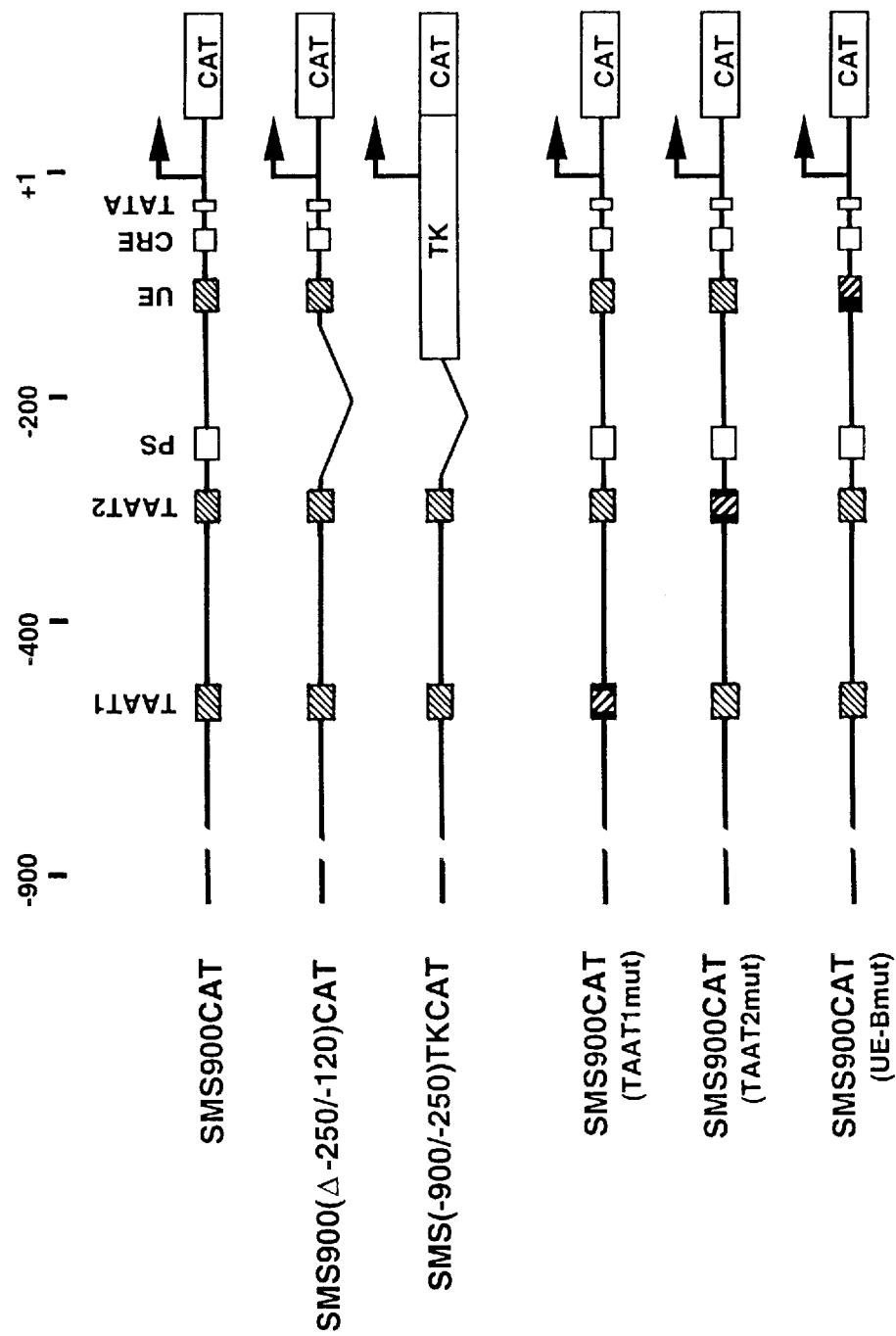
FIG. 7A shows a schematic representation of the somatostatin CAT reporter constructs used in assays whose results are shown in FIGS. 7B and 7C.
Figure 7B:
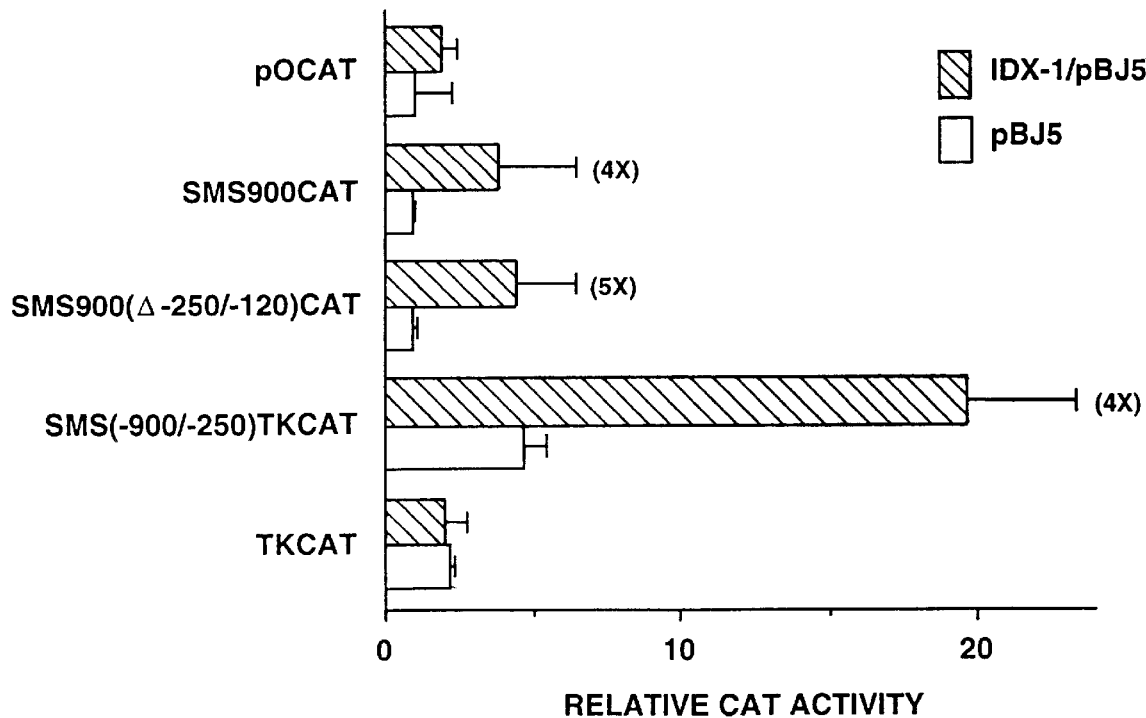
FIG. 7B shows results of transcriptional activation of somatostatin promoter reporter constructs by IDX-1 in which NIH-3T3 cells were cotransfected with an expression vector encoding IDX-1 (IDX-1/pBJ5) and CAT reporter constructs containing portions of the rat somatostatin 5' flanking region.
Figure 7C:
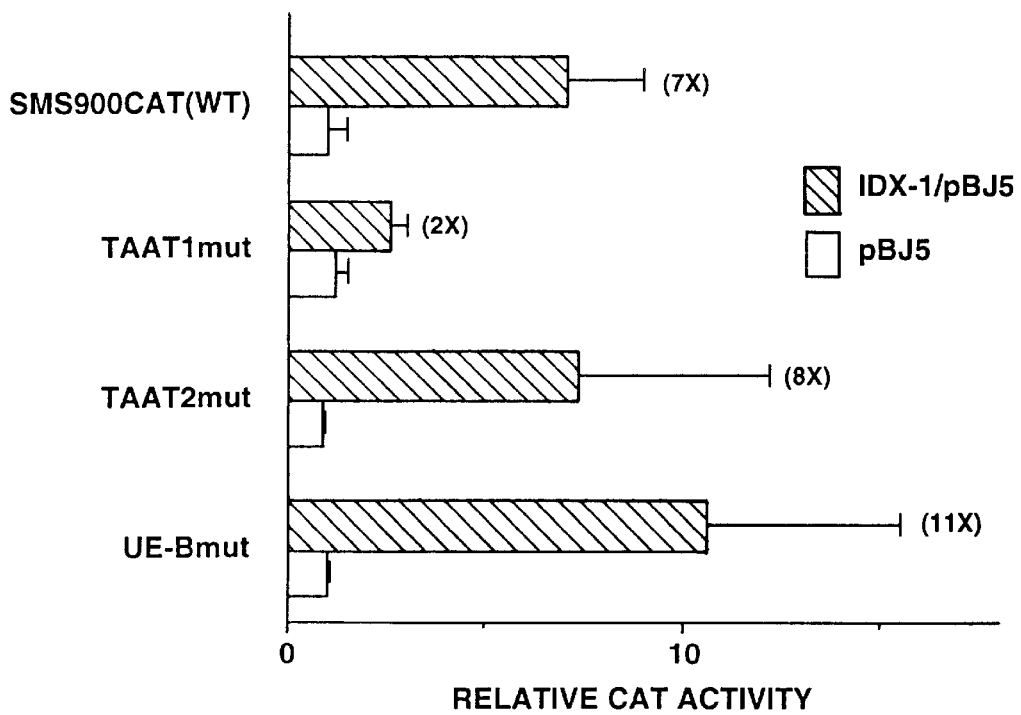
FIG. 7C shows results from cotransfection experiments in NIH-3T3 cells with IDX-1/pBJ5 and the SMS900CAT reporter plasmids containing wild-type or mutated IDX-1 binding sites shown in FIG. 7A.
Figure 7D:
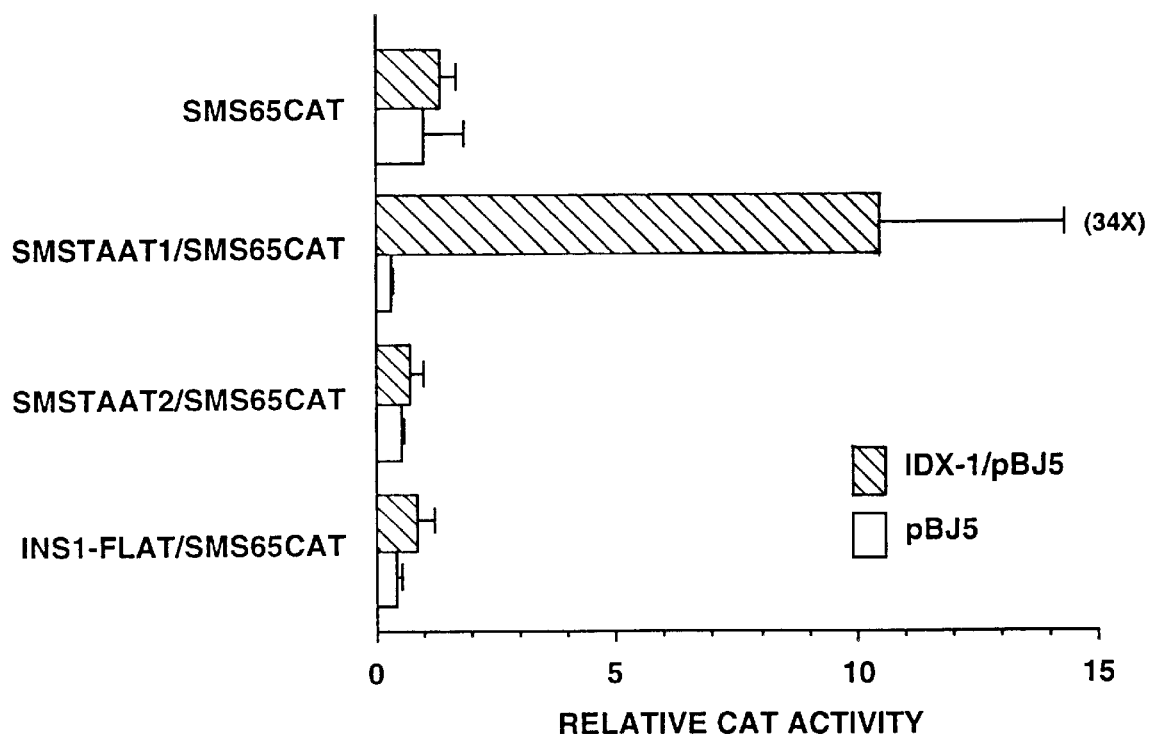
FIG. 7D shows results from cotransfection experiments with IDX-1 binding sites inserted into the plasmid SMS65CAT (Powers et al., 1989, J. Biol. Chem. 264:10048).

IDX-1 activates transcription of the rat somatostatin gene. In contransfection experiments in NIH-3T3 cells, this activation appears to occur mainly through the SMS-TAAT1 element located 450 nucleotides upstream of the transcription start site. Three lines of evidence support this proposal. First, a fragment of the rat somatostatin promoter containing the SMS-TAAT1 and SMS-TAAT2 sequences renders the heterologous TK promoter responsive to transactivation by IDX-1. Second, mutation of SMS-TAAT1 sequence within the SMS900CAT reporter attenuates activation by IDX-1, whereas mutations of the SMS-TAAT2 or SMS-UE-B sites appear not to alter activation. Third, multimerized SMS-TAAT1 sites, but not SMS-TAAT2 sites, are activated by IDX-1. The greater activation of SMS-TAAT1 than SMS-TAAT2 may be related to differences in IDX-1 binding affinities. In EMSA, bacterially-expressed IDX-1 appears to bind SMS-TAAT1 better than SMS-TAAT2 (FIG. 6B). However, IDX-1 also binds well to the INS1-FLAT probe, and weakly activates a reporter construct containing multimerized INS1-FLAT sites (FIG. 7D). The INS1-FLAT site has been shown to be composed of adjacent positive and negative domains such that under certain conditions transcriptional activation requires mutation of the suppressor portion of the element. A similar situation could exist for the SMS-TAAT2 sequence, so that the failure of IDX-1 to transactivate through this element under the conditions used in these experiments should not be interpreted to mean that this site cannot function in transcriptional regulation of the somatostatin gene under other circumstances.

The transcriptional activation activity of IDX-1 was determined as follows. A eukaryotic expression vector for IDX-1 was constructed by inserting the 1.4 kb IDX-1 cDNA into the plasmid pBJ5 (Lin et al., 1990, Science 249:677). Several different reporter constructs were used in cotransfection experiments with IDX-1/pBJ5 expression vector. The SMS900CAT plasmid consists of nucleotides −900 to +54, relative to the transcription start site, of the rat somatostatin gene linked 5' to the coding sequence of the bacterial chloramphenicol acetyl transferase (CAT) gene (Powers et al., 1989, supra). The plasmid SMS900(Δ−250/−120)CAT is identical to SMS900CAT with the exception of an internal deletion between nucleotides −250 and −120. This deletion removes a putative transcriptional suppressor region located between nucleotides −237 and −189 of the rat somatostatin gene (Vallejo et al., in preparation). SMS(−900/−250) TKCAT contains −900 to −250 of the rat somatostatin gene linked 5' to the herpes simplex thymidine kinase promoter in the CAT reporter plasmid PUTKAT (Prost and Moore, 1986, Gene 45:107). The plasmids SMS900CAT(TAAT1mut), SMS900CAT(TAAT2mut) and SMS900CAT(UE-Bmut) were created using oligonucleotide-directed mutagenesis (Kunkel, 1985, Proc. Natl. Acad. Sci. USA 82:488) to introduce clustered nucleotide substitutions in the IDX-1 binding sites located at −450, −290, and —90, respectively, within the SMS900CAT reporter. For SMS-TAAT1, the central 5'-ATTAAT-3' was converted to 5'-GCCGGC-3'. Likewise, SMS-TAAT2 and SMS-UE-B were changed from 5'-TAATTA-3' and 5'-CTAATG-3' to 5'-CGGCCG-3' and 5'-TCGGCA-3', respectively. These mutations abolish IDX-1 binding in EMSA (not shown). Sequences of the mutations were confirmed by dideoxy sequencing. Reporter plasmids were also constructed that contained multimerized-double stranded oligonucleotides corresponding to IDX-1 binding sites (see below for oligonucleotide sequences) inserted into the BamHI sites of the plasmids SMS65CAT (Powers et al., 1989, supra). Sequence, copy number and orientation of the oligonucleotides were confirmed by restriction digest and dideoxy sequencing. The SMSTAAT1/SMS65CAT construct contains six copies of the SMS-TAAT1 oligonucleotide, linked head-to-tail. The SMS-TAAT2/SMS65CAT and INS1-FLAT/SMS65CAT constructs contain three and five head-to-tail copies of their respective oligonucleotides.

NIH-3T3 cells were transfected using CaPO$_4$ (Ausubel et al., 1992, supra) with 5μg of reporter constructs and 5 μg of IDX-1/pBJ5 expression plasmid. Control transfections were performed using pBJ5 with no cDNA insert. Forty-eight hours after transfections, cells extracts were prepared and CAT activities in aliquots of the extracts were determined (Ausubel et al., 1992, supra).

FIG. 7 shows results of transcriptional activation of somatostatin promoter reporter constructs by IDX-1. In FIG. 7A, schematic representation of the somatostatin CAT reporter constructs used in FIGS. 7B and 7C. IDX-1 binding sites identified by EMSA (TAAT1, TAAT2, and UE-B) are shown (closed boxes) along with other known regulatory elements (open boxes) in the rat somatostatin promoter. PS refers to proximal silencer, CRE refers to cyclic AMP response element (Powers et al., 1989, supra), +1 refers to transcription start site, and TK refers to thymidine kinase. Clustered point mutations of SMS-TAAT1, SMS-TAAT2, and SMS-UE-B are designated by cross-hatched boxes. In FIG. 7B, NIH-3T3 cells were cotransfected with an expression vector encoding IDX-1 (IDX-1/pBJ5) and CAT reporter constructs containing portions of the rat somatostatin 5' flanking region. Control transfections were performed using the pBJ5 expression vector lacking a cDNA insert. CAT activities for each experiment were normalized relative to the control values obtained for the parent reporter plasmid pOCAT. Results represent the mean (±SEM) from three or four separate transfections with duplicate plates of cells. Numbers in parentheses indicate fold induction by IDX-1. FIG. 7C shows results from cotransfection experiments in NIH-3T3 cells with IDX-1/pBJ5 and the SMS900CAT reporter plasmids containing wild-type or mutated IDX-1 binding sites shown in FIG. 7A. CAT activities for each experiment were normalized relative to control values obtained for SMS900CAT(WT). FIG. 7D shows results from cotransfection experiments with IDX-1 binding sites inserted into the plasmid SMS65CAT (Powers et al., 1989, supra). CAT activities for each experiment were normalized relative to the control values obtained for SMS65CAT.

Transcriptional activation by IDX-1 was assayed by cotransfection experiments in NIH-3T3 cells with an IDX-1 expression vector (IDX-1/pBJ5) and reporter constructs containing portions of the rat somatostatin 5' flanking region in the plasmid pOCAT (FIG. 7B and C), or multimerized IDX-1 binding sites inserted into the plasmid SMS65CAT (FIG. 7D) (Powers et al., 1989, supra). The SMS900CAT reporter (FIG. 7A) consists of nucleotides −900 to +54 of the rat somatostatin gene linked 5' to the gene encoding the bacterial enzyme chloramphenicol acetyl transferase (CAT). SMS900CAT contains the three IDX-1 binding sites identified by EMSA (SMS-TAAT1, SMS-TAAT2, and SMS-UE-B, FIG. 6B and 6C), and is transactivated by IDX-1 (4-fold, FIG. 7B). IDX-1 also transactivates the reporter plasmid SMS900 (Δ−250/−120)CAT which contains the three IDX-1 binding sites, but lacks transcriptional silencer elements (Vallejo et al., in preparation) located between nucleotides −250 and −120 (5-fold, FIG. 7B). Additional experiments were conducted to determine to what extent the SMS-TAAT1 and SMS-TAAT2 sites contribute to IDX-1 activation of SMS900CAT. First, the −900 to −250 portion of the rat somatostatin gene (containing SMS-TAAT1 and SMS-TAAT2, but not SMS-EU) was inserted upstream of the heterologous thymidine kinase (TK) promoter in the reporter plasmid pUTKAT (Prost and Moore, 1986, supra). This plasmid, SMS(−900/−250)TKCAT, is transactivated by IDX-1 (4-fold, FIG. 7B), whereas the parent plasmid pUTKAT (TKCAT) is not. These results indicate that the −900 to −250 portion of the rat somatostatin gene can confer IDX-1 responsiveness to a heterologous promoter, and are consistent with the proposal that SMS-TAAT1 and/or SMS-TAAT2 may mediate IDX-1 transactivation of SMS900CAT. To further test this hypothesis, nucleotide substitution mutations were introduced into the SMS-TAAT1, SMS-TAAT2, and SMS-EU-B sequences within the SMS900CAT reporter plasmid. As shown in FIG. 7C, the SMS-TAAT1 sequence appears to be required for full activation of SMS900CAT by IDX-1, whereas the SMS-TAAT2 and SMS-UE-B sites are less critical. Finally, in experiments with reporter plasmids containing multimerized IDX-1 binding sites, IDX-1 potently transactivates a reporter construct containing the multimerized SMS-TAAT1 site (34-fold, FIG. 7D) but does not increase transcription of constructs containing multimerized SMS-TAAT2 or INS1-FLAT sequences. Taken together, the results from these cotransfection experiments suggest that IDX-1 transactivates expression of the somatostatin promoter reporter constructs mainly through the upstream SMS-TAAT1 sequence.

Other promoters that are susceptible to IDX-1 transactivation include the insulin and glucagon promoters. In addition, any candidate promoter may be tested for transactivation by IDX-1 by subsituting the candidate promoter for the somatostatin promoter in the CAT reporter system described above.

EXAMPLE III

Other Homeodomain Transcription Factors

Additional homeodomain transcription factors expressed in rat pancreatic islets may be isolated as follows. Rat pancreatic islets were isolated by collagenase digestion and manual selection/transfer (Lacy and Kostianovsky, 1967, Diabetes 16:35). Total RNA was prepared from approximately 2000 islets (Ausubel et al., 1992, supra). First strand cDNA synthesis was performed as described (Ausubel et al., 1992, supra) using 5 $\mu$g islet total RNA and AMV Reverse Transcriptase. One $\mu$l of this cDNA preparation was used as a template for PCR amplification. Amplimer sequences, PCR conditions and subcloning procedures were exactly as described by James and Kazenwadel, (1991, supra). The PCR amplimers contain BamHl or EcoH1 restriction enzyme sites and generate PCR products represent mixed populations of homeodomain cDNA templates. The PCR products represent mixed populations of homeodomain sequences, which were digested with BamH1 and EcoR1, ligated into BamH1/EcoR1-cut pBluescript(KS), and used to transform JM109 bacteria. Individual bacterial colonies were picked, then miniprep plasmid DNAs were prepared and sequenced. Sequences were compared to GenBank entries using the BLAST network service through the National Center for Biotechnology Information (NCBI). Rat islet cDNA preparations were PCR-amplified with degenerate primers designed to anneal to the most highly conserved regions of the Antp homeodomain (PCRHD1 and PCRHD2 in FIG. 8). PCR products were subcloned into pBluescript (KS) and sequenced. Twelve different homeodomain sequences were found among the 80 subclones that were sequenced. The translated amino acid sequences of the twelve homeodomain cDNAs from rat islets are shown in FIG. 8, compared with the corresponding region of the Antp homeodomain with which most share significant homology. Dashes denote sequence identity with the Antp homeodomain shown at the top. Locations of PCRHD1 and PCRHD2 amplimers are shown below. Numbers above Antp sequence indicate amino acid positions within the homeodomain. Also shown are the frequencies of occurrence and closest sequence matches found in Genbank. Frequency of occurrence refers to the number of times a given homeodomain sequence was obtained from sequencing 80 separate DNA minipreps. Numbers in parentheses indicate percent sequence similarity between the sequences amplified from rat islet cDNA and the Genbank entries for previously cloned homeodomains (amino acid similarity; nucleic acid similarity). Sequence #1, which represents greater than 50% of the cloned sequences (45/80), is IDX-1. Sequence comparisons were confined to the regions between amino acids 21–46 of the homeodomain. Genbank searches and sequence comparisons used BLAST software.

FIG. 8 also lists the frequencies of occurrence and highest GenBank similarities for these sequences. Sequence #1 corresponds to the IDX-1 homeodomain and is clearly the most frequently encountered Antp-like homeodomain in rat islet cDNA preparations (45 out of 80 sequences). Ten of the eleven additional sequences are likely to be the rat homologues of previously cloned homeodomain mRNAs. These include Cdx-4 (sequence #16), Hox1.4 (#17), CHox-7 (#22), Hox2.6 (#24), Cdx-3 (#27), Cdx-1 (#35), Hox4.3 (#39), Hox1.11 (#43), Hox4A (#48), and Hoxl.3 (#82). With the exception of Cdx-3 (German et al., 1992, supra), this is the first evidence for expression of these homeodomain mRNAs in rat islets. Sequence #19 currently has no significant matches to sequences contained within GenBank, and appears to represent an additional new rat homeodomain mRNA.

EXAMPLE IV

IDX-1 Promoter Binding Site

IDX-1 binds to a promoter at certain recognition sequences as described herein. Thus, the promoter recognition sequence that IDX-1 binds to will include the sequences: TAATT or TAATG, and more preferably will include the sequences (5'-GATCCTTGTTAATCTAATTACCCTAGGTCTAA-3'); (5'-GATCCCTGATTGCATATTAATTCTCAGATA-3'); (5'-GATCCGATCTCAGTAATTAATCATGCACCA-3');(5'-GATCCGCGAGGCTAATGGTGCGTAAAAGCACTGGTGA-3'); and/or (5'-GATCCAGGCAAGATTATTTGGTCA-3'); or will include sequences common among these nucleotide sequences. Several IDX-1 binding site elements are identified in the rat somatostatin gene promoter and at least one site is identified in the rat insulin 1 gene 5' flanking region. Examination of the sequence of the predicted IDX-1 DNA recognition helix (helix three of the homeodomain) revealed that there is a single amino acid difference between IDX-1 and Antp ($His_{44}$ in IDX-1 vs $Gin_{44}$ in Antp; number refers to position within the homeodomain). Furthermore, $Gin_{44}$ is highly conserved among all Antp-like homeodomains (Scott et al., 1989, supra). This raised the possibility that IDX-1 may have DNA binding properties different from those of other Antp-like homeoproteins. However, results from the EMSA/PCR-based selection and amplification of IDX-1 binding sites (data not shown) and EMSA with several different potential IDX-1 binding sites indicated that IDX-1 has DNA binding specificity similar to other Antp-like homeoproteins (i.e. preference for binding to sites containing a 5'-TAAT(T/G)-3' sequence; Desplan et al., 1988, supra; Scott et al., 1989, supra; Ekker et al., 1991, supra). Thus, it appears that $His_{44}$ does not detectably alter the DNA binding sequence specifity of IDX-1, a finding consistent with studies indicating the apparent unimportance of amino acid residue 44 in homeodomain/DNA interactions (Kissinger et al., 1990, Cell 63:579; Otting et al., 1990, Embo J. 9:3085; Furukubo-Tokunaga et al., 1992, Genes Dev. 6:1082).

EXAMPLE V

Uses

IDX-1 is useful in vitro for producing any desired protein, e.g., human insulin, in which a DNA sequence encoding the protein is under control of the somatostatin promoter. IDX-1 is useful in vivo as a therapeutic agent for administration to a patient afflicted with diabetes.

IDX-1 may be used in vitro as follows. For example, the gene encoding human insulin (GenBank Accession No. J00265, Bell et al., 1980, Nature 284:26) may be joined to the human somatostatin promoter, the construct transfected into a suitable host, e.g., COS cells, along with a construct capable of expressing IDX-1. The cultured cells then will produce IDX-1, and IDX-1 will transactivate the somatostatin promoter, resulting in expression of the insulin gene and production of insulin.

Alternatively, the human insulin gene may be substituted for the CAT gene in the CAT constructs described herein, e.g., the SMSTAATT/SMS65CAT described herein, and IDX-1 used to activate transcription of the insulin construct. Alternatively, the entire insulin gene, including its promoter, may be used, the insulin promoter also being activatable by IDX-1 (see FIG. 7 herein and Ohlsson et al., 1993, Euro. Jour. Mol. Biol. 12:4251). Of course, appropriate secretion signals will be engineered into the construct, if they are not already present, in order to obtain insulin secretion from transfected cells. If desired, the secreted insulin may be purified according to conventional protein purification techniques.

In vivo uses of IDX-1. The IDX-1 gene or protein will have various in vivo uses, as described below.

EXAMPLE VI

Diabetes Treatment Methods

Methods of the invention include administering IDX-1 protein or a variant thereof, DNA encoding IDX-1 or its variant, and IDX-1 protein or a variant in conjunction with an expressible insulin gene, as follows. In each case of IDX-1 administration, IDX-1 is delivered to the patient in an amount sufficient to provide an effective level of endogenous insulin in the patient. An "effective" level of endogenous insulin in a patient refers generally to that level of insulin that is produced endogenously in a healthy patient, i.e., a patient who is not afflicted with diabetes. Alternatively, an "effective" level may also refer to the level of insulin that is determined by the practitioner to be medically effective.

Thus, according to the invention, diabetes may be treated by administering to a patient afflicted with diabetes IDX-1 protein, or a variant thereof, or nucleic acid encoding IDX-1. Optimally, the protein or nucleic acid will be carried by a vehicle, and will be administered in numbers sufficient to provide an effective level of endogenous insulin in the patient.

Treatment methods of the invention will also include administering to a patient IDX-1 protein or an expressible gene encoding IDX-1, or a variant thereof, in conjunction with a construct comprising a promoter recognized by IDX-1 or its variant, e.g., the somatostatin promoter, operationally associated with a gene encoding insulin. The gene encoding IDX-1 and the insulin gene construct may be administered to the patient in the same vehicle or in separate vehicles.

Gene therapy involves the direct manipulation and use of genes to treat disease. The delivery of genes to target cells may be accomplished with relatively high specificity and efficiency according to methods known in the art. There are multiple ways to deliver and express genes as part of a gene therapy protocol. Gene therapy methods known in the art and potentially useful for treatment methods disclosed herein are discussed in Morgan et al., 1993, Ann. Rev. Biochem. 62:191, hereby incorporated by reference.

Genes are introduced into patient's cells so that the recipient cells act as factories within the patient to produce a therapeutically useful protein, e.g., IDX-1. Typically, this process might lead to the replacement of a defective protein, or replenishment of normal proteins which become deficient.

IDX-1 or a variant thereof, or nucleic acid encoding IDX-1 or its variant, may be administered according to the invention as an ex vivo and in vivo therapeutic product. Human somatic gene therapy includes the use of viral or non-viral vectors as vehicles to deliver genes to selected cell populations. Cells may be removed from patients for treatment followed by reimplantation (ex vivo gene manipulation). Alternatively, vectors are directly injected into the patient (in vivo gene manipulation). The goal is to target these genes to a specific cell type in vivo.

The delivery of genes, e.g., the gene encoding IDX-1 alone or in combination with the gene encoding insulin under control of an IDX-1-regulated promoter, to target cells may be accomplished via ex vivo or in vivo methods. Most ex vivo approaches currently being developed require extensive cell separation before the non-specific vector system is applied to the cell population. In vivo approaches eliminate the removal and culturing of patient's cells outside of the body.

The advantages to treating diabetes via gene therapy are as follows. Gene therapy enables the ability to correct diseases such as diabetes, that may result from inherited or acquired genetic defects. Gene therapy can ensure the continuous expression of IDX-1 or a protein under IDX-1 control, e.g., insulin, in the patient's own cells, thus obviating the need for multiple injections and side-effects associated with daily insulin injections. Gene therapy allows for the targeting of a gene to specific cells and the control of expression of a gene to those cells.

The expression of a gene in a target cell may be controlled according to the invention as follows. Gene function, e.g., insulin production, may be deficient in a specific cell type, and the resultant disease, e.g., diabetes mellitus type I or II, correctable if the gene in question is delivered to and expressed in the target cell. Therefore, gene therapy according to the invention, will rely on the promoter transactivating activity of IDX-1; that is, IDX-1 itself may be provided via expression of the IDX-1 gene in target cells, and transactivation of IDX-1-sensitive native promoters such that their associated genes are expressed and the pancreatic insulin-producing β-cell population is increased. Alternatively, the IDX-1 gene may be provided in combination with a gene encoding insulin under control of an IDX-1-sensitive promoter, resulting in IDX-1 transactivation of the insulin gene, and increased levels of insulin.

Target cells useful according to the invention will include, but not be limited to, pancreatic cells, e.g., non-islet pancreatic cells, pancreatic islet cells, islet cells of the β-cell type, non-β-cell islet cells, and pancreatic duct cells. These cell types may be isolated according to methods known in the art for ex vivo manipulation. See, e.g., Githens, 1988, Jour. Pediatr. Gastroenterol. Nutr. 7:486; Warnock et al., 1988, Transplantation 45:957; Griffin et al., 1986, Brit. Jour. Surg. 73:712; Kuhn et al., 1985, Biomed. Biochim. Acta 44:149; Bandisode, 1985, Biochem. Biophys. Res. Comm. 128:396; Gray et al., 1984, Diabetes 33:1055, all of which are hereby incorporated by reference.

The following gene therapy protocols are representative of gene therapy methods useful for accomplishing gene therapy according to the invention, and are not meant to limit the mode by which IDX-1 is useful in gene therapy.

One method for ex vivo delivery of IDX-1 according to the invention is via a ligand/DNA conjugate system as described by Wu, 1987 Jour. Biol. Chem. 262:4429, hereby incorporated by reference. Briefly, DNA encoding IDX-1 in combination with DNA encoding insulin under control of an IDX-1-activatable promoter are encapsulated in a ligand polylysine conjugate to form a ligand-coated DNA particle. The particle then interacts with the ligand receptor on the cell surface, and is taken up by the cell via an endosomal mechanism. Once inside the cell, the endosome is disrupted, and the recombinant genes are expressed in the cell's nucleus. An example of a ligand/receptor pair useful according to the invention is an antibody to the pancreatic β-cell surface antigen p64 in combination with the β-cell surface antigen p64. The p64 antigen is described by Barmeier et at., 1991, Diabetologia 34:727, hereby incorporated by reference. An antibody to the p64 antigen may be made according to conventional monoclonal antibody production protocols, as described herein.

Envelope viruses such as Sendai virus, HIV and influenza infect cells by a process of cell binding followed by virus cell fusion, and the release of nucleocapsid material into the cytoplasm. The process of cell binding and release of viral nucleic acid into the cytoplasm is a function of the viral envelop proteins. Influenza envelope proteins can be reconstituted into lipid vesicles and used to deliver macromolecules into recipient cells with high efficiency. The influenza virus hemagglutinin coat protein (HA) binds to sialic acid residues on the cell surface and is responsible for the process of endosomal escape. The system was first described by Uchida, (1977, Nature 266:839), hereby incorporated by reference, for the deliver of a toxin and has been subsequently modified to deliver DNA to recipient cells with high efficiency (Lapidot, 1990, Experimental Cell Res. 189:241, hereby incorporated by reference).

Alternatively, IDX-1 DNA, alone or in conjunction with an insulin gene that is operationally associated with an IDX-1-activatable promoter, as described herein, may be delivered to a target is-cell as follows. The DNA may be transported via a defective adenovirus, as described in Morgan et al., supra, that contains the promoter and gene of interest along with a pancreatic β-cell targeting antibody; e.g., an antibody to the p64 antigen. The antibody will serve to target the recombinant adenovirus to pancreatic β-cells.

Alternatively, the IDX-1 gene may be directly injected into the pancreas, or a site in the pancreas, either alone or in conjunction with a construct that allows IDX-1-controlled expression of an insulin gene, via microinjection. For example, a surgical opening may be made in a patient afflicted with diabetes, followed by insertion of a 'gene gun' containing the DNA coated with gold particles. The DNA/gold mixture is then microinjected into the pancreas, and the pancreatic cells take up the gold-coated DNA.

Methods for stable transfer of genes into mammalian cells are known in the art, e.g., see Current Protocols in Molecular Biology, 1987, Ausubel et al Eds., John Wiley & Sons, New York, section 9.5.

A treatment for Diabetes mellitus type I, in which there is a deficiency of pancreatic β-cells, may involve converting pancreatic α-cells to β-cells, as follows. Pancreatic α-cells may be converted to β-cells according to the invention by transfecting α-cells with the IDX-1 gene in conjunction with the insulin gene operationally associated with an IDX-1-activatable promoter, e.g., the glucagon promoter. Optionally, additional β-cell factors may be used to aid in converting α to β-cells, e.g., glucokinase, or glucose transporters, as described in Ronner et al., 1993, Diabetes 42:1760, hereby incorporated by reference. The cells are then cultured for a time sufficient to begin production of insulin.

Alternatively, endogenous insulin production may be enhanced using exogenously administered IDX-1. In addition, for diseases that involve overproduction of insulin, e.g., a patient having an insulinoma, an antagonist of IDX-1 may be used to prevent IDX-1-promoted maturation of progenitor cells to β-cells. Antagonists of IDX-1 may include antisense IDX-1 sequences, wherein the antisense sequence is administered to the patient in vivo. Other antagonists to IDX-1 may include anti-IDX-1 antibodies, or ribozymes that are specific for IDX-1 mRNA.

EXAMPLE VII

Diagnostic Kit

The invention also encompasses a diagnostic kit for detecting a defect in a gene encoding IDX-1, comprising: a nucleic acid probe complementary to the native IDX-1 gene, and means for containing the nucleic acid. Diagnosis of a defect in the IDX-1 gene may be indicated by failure of the probe to hybridize under stringent conditions to the IDX-1 sequence in a patient's genomic DNA. Such a probe preferably will be at least 50 nucleotides in length, more preferably on the order of 100–200 nucleotides. The diagnostic kit is useful for identifying defects in the IDX-1 gene in order to identify patients who may benefit from exogenous IDX-1 treatment. Thus, alternatively, the kit may include a nucleic acid probe complementary with a portion of a mutation-containing region of the native IDX-1 gene.

Alternatively, the kit may include a nucleic acid complementary to the native IDX-1 and useful in a polymerase chain reaction-based amplification of test DNA. This type of assay is known as single-strand conformation polymorphism, as described by Orita et al., 1989, Proc. Nat. Aca. Sci. 86:2766, hereby incorporated by reference.

EXAMPLE VIII

Antibodies

1. Production of Monoclonal Antibodies Reactive with IDX-1

A monoclonal antibody reactive with IDX-1 or an IDX-1 variant or portion thereof, may be prepared as described below for preparation of an anti-IDX-1 antibody.

Hybridomas are generated by the fusion of NS-1 myeloma cells with spleen cells obtained from mice immunized with IDX-1 cDNA-transfected COS cells. COS cells may be transfected with the IDX-1 cDNA insert subcloned into a modified CDM8 vector (Aruffo et al., 1987, EMBO J. 6:3313; Tedder et al., 1989, J. Immunol. 143:712) using the DEAE-dextran method as described (Aruffo et al., EMBO J. 6:3313 (1987)). Cell surface expression may be examined after 48 hours by indirect immunofluorescence. Stable cDNA transfected cells are produced using an IDX-1 cDNA cloned into the BamH I site of the retroviral vector pZipNeoSV(X) in the correct orientation (Cepko et al., 1984, Cell 37:1053). The murine pre-B cell line, 300.19, and the human erythroleukemia cell line, K562, are transfected with this vector by electroporation with subsequent selection of stable transfectants using G418 (Gibco/BRL). Cultures of all cell lines are split the day before analysis and were in logarithmic growth.

Anti-IDX-1 mAb are generated by the fusion of NS-1 myeloma cells with spleen cells from BALB/c mice that are repeatedly immunized with COS cells transfected with the IDX-1 cDNA. Each hybridoma is cloned twice and used to generate ascites fluid. The isotypes of the mAb are determined using a mouse monoclonal antibody isotyping kit from Amersham (Arlington Heights, Ill.).

Monoclonal antibodies reactive in indirect immunofluorescence assays with an IDX-1 mRNA positive cell line, but not with an IDX-1 negative cell line, are isolated. The antibodies will not react with untransfected parent cells or cells transfected with vector alone.

Other IDX-1-reactive monoclonal antibodies may be produced using the amino acid sequences disclosed in FIGS. 1–2 GenBank Access. No. V04833, and portions thereof longer than 8–10 amino acids, using conventional monoclonal antibody production methods. Thus, a monoclonal antibody may be made against any epitope of the IDX-1 polypeptide or an IDX-1 mammalian variant or homolog. Preferred IDX-1 epitopes are those occurring between amino acid residues 1–146 and 207–283 of the IDX-1 sequence; i.e., those lying outside of the homeodomain region (146–206).

Mechanism of Action

Without being bound to any one theory, one mechanism of action of IDX-1 may be as follows. IDX-1, found in cells of pancreatic ducts, the progenitor cells for the insulin-producing β-cells, may be involved in regeneration of pancreatic β-cells, i.e., the cells that produce insulin. Analyses of IDX-1 mRNA and protein in rat tissues show that IDX-1 is expressed in pancreatic islets and ducts, and in the duodenum. In electrophoretic mobility shift assays IDX-1 binds to three sites in the 5' flanking region of the rat somatostatin gene. In co-transfection experiments IDX-1 transactivates reporter constructs containing somatostatin promoter sequences, and mutation of the IDX-1 binding sites attenuates transactivation. Reverse transcription-polymerase chain reaction of islet RNA using degenerate amplimers for mRNAs encoding homeoproteins indicates that IDX-1 is the most abundant of twelve different Antp-like homeodomain mRNAs expressed in adult rat islets. The pattern of expression, relative abundance, and transcriptional regulatory activity suggests that IDX-1 may be involved in the regulation of islet hormone genes and in cellular differentiation in the endocrine pancreas and the duodenum. Pancreatic islet cells, or β-cells, may undergo a high degree of turn-over, or apoptosis, resulting in cell death, followed by maturation of new insulin-producing β-cells. In Diabetes type I afflicted patients, islet cell turn-over may be increased or new islet cell maturation may be compromised, resulting in a deficit of insulin-producing cells. Thus, methods of the invention for treating Diabetes mellitus type I may compensate for a deficit of insulin-producing cells by IDX-1-promoted islet-β-cell replenishment. In Diabetes type II afflicted patients, where β-cells are present but may also contain a defect, insulin production may be promoted directly using IDX-1 and a recombinant insulin gene, or indirectly by promoting β-cell proliferation.

IDX-1 may be a master transcription factor affecting numerous genes in pancreatic cells. For example, IDX-1 activates both the somatostatin and insulin promoters, yet somatostatin normally inhibits the production and secretion of insulin. It appears that IDX-1 thus regulates genes having differing regulatory pathways, e.g., somatostatin, insulin, and glucagon. IDX-1 thus may work in conjunction with other regulatory factors.

EXAMPLE IX

Transgenic Mice

Transgenic animals containing an IDX-1 transgene are useful as models for either diabetes mellitus type I or II. For example, this type of transgenic animal is most useful as an animal model for agents and procedures useful in treating or diagnosing diabetes in humans. Treatments that potentially cure this disease, or relieve its symptoms, may be tested first in a transgenic animal which exhibits symptoms of diabetes by administering the potential treatment to the animal and observing the effects, and comparing the treated animals to untreated controls.

Transgenic mice may be produced in which IDX-1 is ectopically expressed in the exocrine pancreas, pancreatic islet α-cells, and the jejunum. The IDX-1 cDNA may be linked to promoters that drive tissue-specific expression in these three tissues. The recombinant transgenes may be introduced into one-cell mouse embryos that are then allowed to develop through birth to sexual maturation.

Bredding of these mice and analyses of their offspring will allow evaluation of the effects of expression of IDX-1 in sites where it is not normally detected.

1. Preparation of Transgenes.

Transgenes will be constructed that contain the IDX-1 cDNA and promoter/enhancer regions from the elastase, glucagon or intestinal fatty acid binding protein genes. The IDX-1 cDNA has been subcloned into the XbaI site in the polylinker of pBluescript SK(−). Promoter/enhancer fragments will be excised from their respective plasmids and inserted, in the proper orientation, upstream of the IDX-1 coding sequences. Additionally, a fragment of the rabbit beta globin gene containing exon 2, intron 2 and part of exon 3 (Nishi et al., 1988, Nature 331:267) will be inserted between the promoter/enhancer regions and the IDX-1 cDNA to decrease the likelihood for incorrect internal splicing leading to truncated IDX-1 mRNA production. An additional fragment of the rabbit beta globin gene, containing exon 3 with the polyadenylation signal, will be inserted 3' to the IDX-1 cDNA to ensure that the IDX-1 mRNA produced by transcription of the transgenes will be correctly terminated and polyadenylated. Fragments that contain the promoter/enhancers, beta globin splicing and polyadenylation sequences, and IDX-1 coding sequences will be excised from the recombinant plasmids and prepared for microinjection as described by Hogan et al, (1986, Manipulating the Mouse Embryo: A Laboratory Manual, Cold Spring Harbor Laboratory, CSH, N.Y.). All recombinant DNA methods will be performed according to standard procedures (Maniatis et al., 1989, Molecular Cloning: A Laboratory Manual. Cold Spring Harbor Laboratory Press, CSH, N.Y.).

A transgene will be constructed that contains 2.1 Kb of the rat glucagon gene (Lee et al., 1992, J. Biol. Chem. 267:10705), the IDX-1 cDNA, and the beta globin splicing and polyadenylation sequences. The 2.1 Kb rat glucagon gene fragment contains approximately 2.0 kB of 5' flanking sequences and 58 bp of exon 1. This promoter fragment directs expression of SV40 large T antigen coding sequences in pancreatic α-cells, in certain brain regions, and in enteroendocrine cells throughout the gastrointestinal tract. Use of this transgene will allow examination of the effects of ectopic expression of IDX-1 in pancreatic islet alpha cells and throughout the gut. Prior to production of transgenic mice, the Glu/IDX transgene will be transfected into the glucagon-producing hamster cell line In R1G9. Nuclear extracts will be prepared from the transfected cells (Schreiber et al., 1989, Nucl. Acids Res. 17: 6419) and analyzed by Western immunoblot (Miller et al., 1994, Embo J., in press) and electrophoretic mobility shift assay (Miller et al., 1993, Mol. Cell. Biol 13:7080) to confirm that the transgene expresses a functional IDX-1 protein.

To drive ectopic expression of IDX-1 in pancreatic acinar cells, a transgene will be constructed that contains a fragment of the rat elastase gene 5' flanking region (−500 to +8), the IDX-1 cDNA, and the beta globin splicing and polyadenylation sequences. The elastase promoter fragment has been shown to direct expression of human growth hormone coding sequences exclusively within the exocrine pancreas (Ornitz et al., 1985, Nature 313:600). Prior to generation of transgenic mice, the Elas/IDX transgene will be tested by transfection into the hamster pancreatic acinar cell line, AR42J.

A transgene will be constructed which contains a fragment of the mouse intestinal fatty acid promoter (I-FABP) 5' flanking region (−1178 to +28), the IDX-1 cDNA, and the beta globin sequences described above. The I-FABP promoter has been shown to drive expression of human growth hormone coding sequences in the duodenum, jejunum and ileum (Cohn et al., 1992, J. Cell. Biol. 119: 27). This transgene will be used to create transgenic mice in which IDX-1 expression will be extended further along the duodenal-clonic axis to the jejunum and ileum. Prior to production of transgenic mice, the I-FABP/IDX transgene will be tested by transfection into human intestinal Caco-2 cells.

2. Generation of Transgenic Mice.

All of the initial animal work associated with the generation of transgenic mice will be performed at the Beth Isreal Hospital Transgenic Facility (BITF). The BITF maintains a colony to transgenic mouse production that includes female mice for matings to produce fertilized eggs, fertile stud male mice, sterile stud male mice for the production of pseudopregnant females, and female mice to serve as pseudopregnant recipients and foster mothers. All of the preliminary animal manipulations, including generation of super-ovulating females and pseudopregnant females, vasectomizing males, recovery of one-celled embryos, microinjection of DNA into pronuclei, and reimplantation of embryos will be performed by standard procedures that are currently being used at the BITF (Gordon and Ruddel, 1983, Methods Enzymol. 101:411; Hogan et al., 1986, Manipulating the Mouse Embryo, Cold Spring Harbor Laboratory). For production of one-celled preimplantation embryos, super-ovulating immature female FVB/N mice will be mated overnight with fertile random-bred Swiss ICR male mice. The same night, pseudopregnant female recipients will be produced by mating mature female Swiss ICR mice with vasectomized males. The following morning immature female mice displaying vaginal plugs will be sacrificed by cervical dislocation for recovery of one-celled embryos. Transgene DNA will be microinjected into the pronuclei of the embryos, which will then be implanted into the oviducts of the pseudopregnant mature female mice. Noon of the day of injection is designated as 0.5 days post-coitum (dpc). Litters will be allowed to develop in utero until 18.5 dpc, at which time embryos will be analyzed for transgenic incorporation and expression, and for developmental abnormalities as described below.

3. Analyses of Transgenic Mice.

At 18.5 dpc, mothers will be sacrificed by asphyxiation with carbon dioxide, and the fetuses will be delivered by caesarian section. Genotypes of embryos will be determined by PCR/Southern Blot hybridization analysis of genomic DNA prepared from extra-embryonic tissues (yolk sac) or embryonic tails (Laird et al., 1991, Nucl. Acids Res. 19:4293). The PCR amplimers will be designed to anneal to sequences within the beta globin intron and the coding portion of the IDX-1 cDNA to yield a unique amplification product for DNA samples from mice incorporating the transgene. Aliquots of the PCR products will be analyzed by Southern Blot hybridization using an oligonucleotide probe complementary to sequences in the 5' untranslated region of the IDX-1 cDNA. After taking DNA samples for PCR/Southern Blot genotype analysis, embryos will be fixed in 4% paraformaldehyde in phosphate-buffered saline at 4° C. overnight, dehydrated in graded alcohols, and stored at −20° C. Dehydrated embryos will be transferred into xylene and embedded in paraffin. To analyze transgene expression, fetal sections (7 μm) will be used for in situ hybridization using IDX-1 specific cRNA probes (Simmons et al., 1989, J. Histotechnology 12:169; Hogan et al, 1986, supra), or immunohistochemistry with IDX-1 antiserum (Miller et al., 1994, supra). If necessary, expression of transgenes will be examined (or confirmed) by RT-PCR or RNase protection analyses (Ausubel et al., 1992, Short Protocols in Molecular Biology, second edition) of RNA samples from dissected fetal tissues using transgene-specific PCR amplimers and probes, or cRNA probes. Fetuses appropriately expressing the transgenes will be further analyzed for developmental abnormalities in the regions of ectopic IDX-1 expression. Non-transgenic littermates will be analyzed in parallel for comparison. For all of the transgenic embryos, sections containing tissues in which the transgenes are expressed will first be analyzed for morphological alterations by staining with hematoxylin and eosin. Additionally, immunohistochemistry and in situ hybridization will be performed with selected antisera and cRNA probes. For Glu/IDX transgenic embryos, sections containing embryonic pancreas and intestine will be analyzed using antisera or cRNA probes for insulin, somatostatin and glucagon. For Elas/IDX transgenic embryos, sections containing embryonic pancreas will be analyzed for insulin, glucagon, somatostatin and for exocrine pancreas-specific markers such as trypsin and chymotrypsin. For I-FAEP/IDX transgenic embryos sections containing fetal duodenum, jejunum and ileum will be analyzed for insulin, somatostatin, and glucagon, and intestinal markers (e.g. sucrase-isomaltase; Leeper and Henning, 1990, Am. J. Physiol. 258:G52), which under normal circumstances have distinct domains of expression along the duodenal-colonic axis.

4. Loss of Function/Targeted Disruption Studies

To determine if IDX-1 expression is required for normal development of the pancreas and duodenum, mice will be created in which both alleles of the IDX-1 gene have been inactivated by homologous recombination in embryonic stems (ES) cells. The development of this technique has been a major breakthrough in the analysis of gene function during embryonic development and in adult animals. ES cells are derived from the inner cell mass of mouse blastocysts, and have the ability to contribute to all cell lineages in the body, including germ cells. ES cell lines are now available that are fully pluripotent, and it is readily possible to inactivate or alter specific genes in ES cells by homologous recombination (Mansour et al., 1988, Nature 336:348). Genetically modified ES cells can be injected into mouse blastocysts to generate chimeric mice, which contain cells derived from their own stem cells as well as from the injected, modified stem cells. When some of the germ cells from the chimeric mice are derived from the modified stem cells, the modified gene can be passed to the offspring of the chimeric animal, leading to inheritance of the altered gene. When chimeric males are bred with normal female mice, those males in which the modified gene is present in germ cells will produce some offspring that are heterozygous for the altered gene. These offspring (F1) can serve as heterozygous founders for generating offspring (F2) homozygous for the modified gene. The effects of modifying the gene are analyzed in F2 homozygous mutant mice. This is the overall strategy that will be employed for inactivation of the mouse IDX-1 gene.

(a) Cloning the mouse IDX-1 gene and constructing a targeting vector for homologous recombination in ES cell.

The mouse IDX-1 gene may be used in construction of the targeting vector for homologous recombination in ES cells. A mouse genomic library has been screened at moderate stringency with the cDNA encoding rat IDX-1. Ten separate phage clones have been plaque purified. Characterization of these putative IDX-1 genomic fragments will determine the exact strategy to be used for construction of the targeting vector. The mouse genomic library (SV129/Lambda DASHII, Strategene) was used. It is desirable to isolate the mouse IDX-1 gene from the SV129 mouse strain, as this is the same mouse strain from which the ES cells are derived. Targeting efficiency is believed to be higher when the genomic portions of the targeting vector and the ES cells are from the same mouse strain. The targeting vector will contain an IDX-1 genomic fragment with the following features: 1) it will be as large as possible, 2) the IDX-1 coding sequences will not be located too close to either end, and 3) a neomycin (neo) resistance cassette (Mansour et al., 1988, supra) will be inserted within the IDX-1 coding region so that the open reading frame will be disrupted, producing a truncated and non-functional protein. The targeting vector will also contain at least one copy of the pMCI-HSVTK cassette (Mansour et al., 1988, supra) which will be attached to the 3' end of the IDX-1 genomic fragment. After electroporation of the targeting vector into ES cells, cells will be cultured in the presence of the nucleotide analog gancyclovir and the neomycin derivative G418. This will permit selection for cells having undergone homologous recombination events at the IDX-1 gene loci, relative to those in which the entire targeting vector has been incorporated into the genome through random integration. In random integration events, both the neo resistance gene will allow the cells to grow in the presence of G418, while incorporation of the HSVTK sequences will confer sensitivity to gancyclovir. For true gene targeting events, the neo resistance gene will be substituted for coding portions of the IDX-1 gene, while the HSVTK portion of the targeting vector will be lost. These cells will be resistant to G418 and gancyclovir. This "positive and negative selection", first proposed by Mansour et al (1988, supra), greatly favors the growth and clonal expansion of ES cells which have undergone true homologous recombination at the correct locations, relative to those having undergone random incorporation of the targeting vector.

(b) Electroporation, selection and analysis of ES cells.

J-1 ES cells from SV129 mice will be electroporated with 25μg of linearized, purified targeting vector DNA. Electroporated cells will be allowed to recover under non-selective conditions for 24 hr., then will be cultured for 6 to 10 days int he presence of G418 and gancyclovir as described by Ramirez-Solis et al. (1993, Cell 73:279). Surviving colonies will be individually picked and transferred to duplicate multiwell plates for propagation and analysis of IDX-1 genomic targeting events. To screen colonies for homologous recombination at the IDX-1 genomic loci, DNA will be isolated from ES cell lines and analyzed by PCR and Southern Blot Hybridization. PCR amplimers will be designed to anneal to sequences within the IDX-1 genomic fragment and within the neomycin resistance cassette to yield different sized products for normal and mutated IDX-1 alleles. Aliquots of the amplification reaction products will be fractionated on agarose gels, transferred to nitrocellulose, and hybridized with a radioactive oligonucleotide probe corresponding to IDX-1 sequences outside of the region removed by substitution of the neomycin cassette. PCR-positive clones will be confirmed by genomic Southern analysis. DNA samples will be digested with enzymes selected to cleave the IDX-1 gene in regions outside of the targeted mutation to yield fragments of different sized for normal and mutated alleles. The samples will be analyzed by Southern blot hybridization analysis using oligonucleotide probes that recognize DNA sequences within the IDX-1 genomic fragment or the neomycin resistance cassette.

c) Blastocyst injection and mouse breeding.

Groups of targeted ES cells will be injected into the blastocele of 3.5 days post-coitum (dpc) C57B1/6 blastocysts. The injected blastocysts will be transferred to pseudopregnant female Swiss (ICR) mice and allowed to develop to term. The extent of chimerism will be determined by the degree of agouti coat color (from the SV129 ES cells) contribution tot he fur at one week of age. Male chimeras will be bred to C57B1/6 female mice to determine their potential for germline transmission, which will be estimated by agouti coat color in the progeny. Fl animals heterozygous for the mutated IDX-1 allele will be interbred to generate F2 mice homozygous for the inactivated IDX-1 gene.

d) Mouse DNA analysis.

To determine the genotypes of embryonic mice, genomic DNA will be extracted from tail clips or yolk sacs as described by Ramirez-Solis et al. (1993, supra), and analyzed by PCR and Southern blot hybridization as described above for genotype analysis of ES cell lines. For genotypic analysis of young mice, DNA will be extracted from tail or ear pieces.

e) Analyses of phenotypic alterations in mice homozygous for the inactivated IDX-1 gene.

Embryos will be delivered at 18.5 dpc by caesarian section and fixed overnight at 4° C. in 4% paraformaldehyde in phosphate-buffered saline. Fixed embryos will be dehydrated in graded alcohols, embedded in paraffin, sectioned at 6–10 μm, and stained with hematoxylin and eosin. Particular attention will be devoted to analysis of the pancreas and small intestine. Additionally, sections of the embryos will be analyzed using immunohistochemistry and in situ hybridization using antisera or cRNA probes to detect markers for pancreatic and duodenal function. These include the major islet hormones insulin, glucagon and somatostatin, exocrine pancreatic markers such as chymotrypsin, trypsin and elastase, and the intestinal proteins sucrase-isomaltase, and I-FABP. Antisera or cDNAs to generate CRNA probes have been obtained, or are available for each of these markers.

Transgenic mice of this invention also can be used as a source of cells for cell culture. Tissues of transgenic mice are analyzed for the presence of the activated recombinant gene, either by directly analyzing DNA or RNA, or by assaying the tissue for the protein expressed by the gene. Cells of tissues carrying the gene can be cultured, using standard tissue culture techniques, and used, e.g., to study the causes of diabetes mellitus type I or II at the cellular and tissue levels.

OTHER EMBODIMENTS

Other embodiments will be evident to those of skill in the art. It should be understood that the foregoing detailed description is provided for clarity only and is merely exemplary. The spirit and scope of the present invention are not limited thereto, being defined by the claims set forth below.

We claim:

1. A recombinant polypeptide that transactivates the somatostatin promoter, the natural analog of the polypeptide being present in pancreatic duct cells and not present in pancreatic α-cells, the polypeptide being encoded by a gene which encodes a protein on the order of 31 kd.

2. A recombinant protein comprising the amino acid sequence of IDX-1.

3. A method of treating diabetes comprising administering to a patient in need thereof a recombinant polypeptide that transactivates the somatostatin promoter, the natural analog of said polypeptide being present in pancreatic duct cells and not present in pancreatic α-cells, the polypeptide being encoded by a gene which encodes a protein on the order of 31 kd, the polypeptide being administered in an amount and for a time sufficient to provide an effective level of endogenous insulin in the patient.

4. The method of claim 3, said recombinant polypeptide being encoded by the nucleic acid sequence of SEQ ID NO: 1.

5. The method of claim 4, said recombinant polypeptide being IDX-1.

6. A recombinant polypeptide that transactivates the somatostatin promoter, the natural analog of the polypeptide being present in pancreatic β-cells and not present in pancreatic α-cells, the polypeptide being encoded by a gene which encodes a protein on the order of 31 kd.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 1403 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 101..949

( x i ) SEQUENCE DESCRIPTION: SEQ ID NO:1:

```
GAATTCCGGG  GCGCTGAGAG  TCCGTGAGCT  GCCCAGCGCC  TAAGGCCTGG  CTTGTAGCTC              60

CCTACCCCGG  GCTGCCGGCC  CCGAAGTGCC  GGCTGCCACC  ATG  AAT  AGT  GAG  GAG             115
                                                 Met  Asn  Ser  Glu  Glu
                                                  1                    5

CAG  TAC  TAC  GCG  GCC  ACA  CAG  CTC  TAC  AAG  GAC  CCG  TGC  GCA  TTC  CAG     163
Gln  Tyr  Tyr  Ala  Ala  Thr  Gln  Leu  Tyr  Lys  Asp  Pro  Cys  Ala  Phe  Gln
                     10                    15                     20

AGG  GGT  CCG  GTG  CCA  GAG  TTC  AGT  GCT  AAT  CCC  CCT  GCG  TGC  CTG  TAC     211
Arg  Gly  Pro  Val  Pro  Glu  Phe  Ser  Ala  Asn  Pro  Pro  Ala  Cys  Leu  Tyr
                 25                    30                     35

ATG  GGC  CGC  CAG  CCC  CCA  CCT  CCG  CCG  ACA  CCC  AGT  TTT  GCA  GGC  TCG     259
Met  Gly  Arg  Gln  Pro  Pro  Pro  Pro  Pro  Thr  Pro  Gln  Phe  Ala  Gly  Ser
```

| | | | | | | | | | | | | | | | | |
|---|---|---|---|---|---|---|---|---|---|---|---|---|---|---|---|---|
| | | 40 | | | | | 45 | | | | | 50 | | | | |
| CTG | GGA | ACG | CTG | GAA | CAG | GGA | AGT | CCC | CCG | GAC | ATC | TCC | CCA | TAC | GAA | 307 |
| Leu | Gly | Thr | Leu | Glu | Gln | Gly | Ser | Pro | Pro | Asp | Ile | Ser | Pro | Tyr | Glu | |
| | 55 | | | | | 60 | | | | | 65 | | | | | |
| GTG | CCC | CCG | CTC | GCC | GAT | GAC | CCG | GCT | GGC | GCG | CAC | CTC | CAC | CAC | CAC | 355 |
| Val | Pro | Pro | Leu | Ala | Asp | Asp | Pro | Ala | Gly | Ala | His | Leu | His | His | His | |
| 70 | | | | | 75 | | | | | 80 | | | | | 85 | |
| CTC | CCA | GCT | CAG | CTC | GGG | CTC | GCC | CAT | CCA | CCT | CCC | GGA | CCT | TTC | CCG | 403 |
| Leu | Pro | Ala | Gln | Leu | Gly | Leu | Ala | His | Pro | Pro | Pro | Gly | Pro | Phe | Pro | |
| | | | | 90 | | | | | 95 | | | | | 100 | | |
| AAT | GGA | ACC | GAG | ACT | GGG | GGC | CTG | GAA | GAG | CCC | AGC | CGC | GTT | CAT | CTC | 451 |
| Asn | Gly | Thr | Glu | Thr | Gly | Gly | Leu | Glu | Glu | Pro | Ser | Arg | Val | His | Leu | |
| | | | 105 | | | | | 110 | | | | | 115 | | | |
| CCT | TTC | CCG | TGG | ATG | AAA | TCC | ACC | AAA | GCT | CAC | GCG | TGG | AAA | AGC | CAG | 499 |
| Pro | Phe | Pro | Trp | Met | Lys | Ser | Thr | Lys | Ala | His | Ala | Trp | Lys | Ser | Gln | |
| | | 120 | | | | | 125 | | | | | 130 | | | | |
| TGG | GCA | GGA | GGT | GCA | TAC | GCA | GCA | GAA | CCG | GAG | GAG | AAT | AAG | AGG | ACC | 547 |
| Trp | Ala | Gly | Gly | Ala | Tyr | Ala | Ala | Glu | Pro | Glu | Glu | Asn | Lys | Arg | Thr | |
| | 135 | | | | | 140 | | | | | 145 | | | | | |
| CGT | ACA | GCC | TAC | ACT | CGG | GCC | CAG | CTG | CTG | GAG | CTG | GAG | AAG | GAA | TTC | 595 |
| Arg | Thr | Ala | Tyr | Thr | Arg | Ala | Gln | Leu | Leu | Glu | Leu | Glu | Lys | Glu | Phe | |
| 150 | | | | | 155 | | | | | 160 | | | | | 165 | |
| TTA | TTT | AAC | AAA | TAC | ATC | TCC | CGG | CCT | CGC | CGG | GTG | GAG | CTG | GCA | GTG | 643 |
| Leu | Phe | Asn | Lys | Tyr | Ile | Ser | Arg | Pro | Arg | Arg | Val | Glu | Leu | Ala | Val | |
| | | | | 170 | | | | | 175 | | | | | 180 | | |
| ATG | CTC | AAC | TTG | ACT | GAG | AGA | CAC | ATC | AAA | ATC | TGG | TTC | CAA | AAC | CGT | 691 |
| Met | Leu | Asn | Leu | Thr | Glu | Arg | His | Ile | Lys | Ile | Trp | Phe | Gln | Asn | Arg | |
| | | | 185 | | | | | 190 | | | | | 195 | | | |
| CGC | ATG | AAG | TGG | AAG | AAA | GAG | GAA | GAT | AAG | AAA | CGT | AGT | AGC | GGG | ACA | 739 |
| Arg | Met | Lys | Trp | Lys | Lys | Glu | Glu | Asp | Lys | Lys | Arg | Ser | Ser | Gly | Thr | |
| | | 200 | | | | | 205 | | | | | 210 | | | | |
| ACG | AGC | GGG | GGC | GGT | GGG | GGC | GAA | GAG | CCG | GAG | CAG | GAT | TGT | GCC | GTA | 787 |
| Thr | Ser | Gly | Gly | Gly | Gly | Gly | Glu | Glu | Pro | Glu | Gln | Asp | Cys | Ala | Val | |
| | 215 | | | | | 220 | | | | | 225 | | | | | |
| ACC | TCG | GGC | GAG | GAG | CTG | CTG | GCA | TTG | CCA | AAG | CCA | CCA | CCT | CCC | GGA | 835 |
| Thr | Ser | Gly | Glu | Glu | Leu | Leu | Ala | Leu | Pro | Lys | Pro | Pro | Pro | Pro | Gly | |
| 230 | | | | | 235 | | | | | 240 | | | | | 245 | |
| GGT | GTT | GTG | CCC | TCA | GGC | GTC | CCT | GCT | GCT | GCC | CGG | GAG | GGC | CGA | CTG | 883 |
| Gly | Val | Val | Pro | Ser | Gly | Val | Pro | Ala | Ala | Ala | Arg | Glu | Gly | Arg | Leu | |
| | | | | 250 | | | | | 255 | | | | | 260 | | |
| CCT | TCC | GGC | CTT | AGT | GCG | TCC | CCA | CAG | CCC | TCC | AGC | ATC | GCG | CCA | CTG | 931 |
| Pro | Ser | Gly | Leu | Ser | Ala | Ser | Pro | Gln | Pro | Ser | Ser | Ile | Ala | Pro | Leu | |
| | | | 265 | | | | | 270 | | | | | 275 | | | |
| CGA | CCG | CAG | GAA | CCC | CGG | TGAGGACCGC | | AGGCTGAGGG | | TGAGCGGGTC | | | | | | 979 |
| Arg | Pro | Gln | Glu | Pro | Arg | | | | | | | | | | | |
| | | | 280 | | | | | | | | | | | | | |

| | | | | | |
|---|---|---|---|---|---|
| TGGGACCCAG | AGTGCGGACA | TGGGCATGGG | CCCGGGCAGC | TGGATAAGGG | AGGGGATCAT | 1039 |
| GAGGCTTAAC | CTAAACGCCA | CACACAAGGA | GAACATTCTT | CTTGGGGGCA | CAAGAGCCAG | 1099 |
| TTGGGTATAC | CAGCGAGATG | CTGGCAGACC | TCTGGGAAAA | AAAAAGACCC | GAGCTTCTGA | 1159 |
| AAACTTTGAG | GCTGCCTCTC | GTGCCATGTG | AACCGCCAGG | TCTGCCTCTG | GGACTCTTTC | 1219 |
| CTGGGACCAA | TTTAGAGAAT | CAGGCTCCCA | ACTGAGGACA | ATGAAAGGT | TACAAACTTG | 1279 |
| AGCGGTCCCA | TAACAGCCAC | CAGGCGAGCT | GGACCGGGTG | CCTTTGACTG | GTCGGCCGAG | 1339 |
| CAATCTAAGG | TTGAGAATAA | AGGGAGCTGT | TGAGGTTTC | AAAAAAAAA | AAAAACCGGA | 1399 |
| ATTC | | | | | | 1403 |

( 2 ) INFORMATION FOR SEQ ID NO:2:

(i) SEQUENCE CHARACTERISTICS:
(A) LENGTH: 283 amino acids
(B) TYPE: amino acid
(D) TOPOLOGY: linear (ii) MOLECULE TYPE: protein (xi) SEQUENCE DESCRIPTION: SEQ ID NO:2:

```
Met Asn Ser Glu Glu Gln Tyr Tyr Ala Ala Thr Gln Leu Tyr Lys Asp
 1               5                  10                  15
Pro Cys Ala Phe Gln Arg Gly Pro Val Pro Glu Phe Ser Ala Asn Pro
                20                  25                  30
Pro Ala Cys Leu Tyr Met Gly Arg Gln Pro Pro Pro Pro Pro Thr Pro
                35                  40                  45
Gln Phe Ala Gly Ser Leu Gly Thr Leu Glu Gln Gly Ser Pro Pro Asp
            50                  55                  60
Ile Ser Pro Tyr Glu Val Pro Pro Leu Ala Asp Asp Pro Ala Gly Ala
 65                  70                  75                  80
His Leu His His His Leu Pro Ala Gln Leu Gly Leu Ala His Pro Pro
                    85                  90                  95
Pro Gly Pro Phe Pro Asn Gly Thr Glu Thr Gly Gly Leu Glu Glu Pro
               100                 105                 110
Ser Arg Val His Leu Pro Phe Pro Trp Met Lys Ser Thr Lys Ala His
           115                 120                 125
Ala Trp Lys Ser Gln Trp Ala Gly Gly Ala Tyr Ala Ala Glu Pro Glu
130                 135                 140
Glu Asn Lys Arg Thr Arg Thr Ala Tyr Thr Arg Ala Gln Leu Leu Glu
145                 150                 155                 160
Leu Glu Lys Glu Phe Leu Phe Asn Lys Tyr Ile Ser Arg Pro Arg Arg
               165                 170                 175
Val Glu Leu Ala Val Met Leu Asn Leu Thr Glu Arg His Ile Lys Ile
           180                 185                 190
Trp Phe Gln Asn Arg Arg Met Lys Trp Lys Lys Glu Glu Asp Lys Lys
       195                 200                 205
Arg Ser Ser Gly Thr Thr Ser Gly Gly Gly Gly Glu Glu Pro Glu
   210                 215                 220
Gln Asp Cys Ala Val Thr Ser Gly Glu Glu Leu Leu Ala Leu Pro Lys
225                 230                 235                 240
Pro Pro Pro Pro Gly Gly Val Val Pro Ser Gly Val Pro Ala Ala Ala
               245                 250                 255
Arg Glu Gly Arg Leu Pro Ser Gly Leu Ser Ala Ser Pro Gln Pro Ser
           260                 265                 270
Ser Ile Ala Pro Leu Arg Pro Gln Glu Pro Arg
       275                 280
```

(2) INFORMATION FOR SEQ ID NO:3:

(i) SEQUENCE CHARACTERISTICS:
(A) LENGTH: 61 amino acids
(B) TYPE: amino acid
(D) TOPOLOGY: linear (ii) MOLECULE TYPE: peptide (iii) HYPOTHETICAL: NO (iv) ANTI-SENSE: NO (v) FRAGMENT TYPE: internal -continued ( x i ) SEQUENCE DESCRIPTION: SEQ ID NO:3:

Glu Arg Lys Arg Gly Arg Gln Thr Tyr Thr Arg Tyr Gln Thr Leu Glu
1               5                   10                  15

Leu Glu Lys Glu Phe His Phe Asn Arg Tyr Leu Thr Arg Arg Arg Arg
            20                  25                  30

Ile Glu Ile Ala His Ala Leu Cys Leu Thr Glu Arg Gln Ile Lys Ile
        35                  40                  45

Trp Phe Gln Asn Arg Arg Met Lys Trp Lys Lys Glu Asn
    50                  55                  60

( 2 ) INFORMATION FOR SEQ ID NO:4:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

Xaa Xaa Leu Xaa Xaa Lys Xaa Ile Ser Xaa Pro Xaa Xaa Val Xaa Leu
1               5                   10                  15

Xaa Val Met Xaa Asn Xaa Xaa Xaa Xaa His Xaa Xaa Xaa Xaa Xaa Xaa
            20                  25                  30

Xaa Xaa Xaa Xaa Xaa Xaa Xaa Xaa Xaa Glu
        35                  40

( 2 ) INFORMATION FOR SEQ ID NO:5:

( i ) SEQUENCE CHARACTERISTICS:
        ( A ) LENGTH: 60 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

Asn Xaa Xaa Thr Xaa Thr Ala Xaa Ser Xaa Ser Xaa Leu Xaa Xaa Xaa
1               5                   10                  15

Xaa Xaa Xaa Xaa Xaa Xaa Asp Lys Xaa Ile Ser Xaa Pro Xaa Xaa Val
            20                  25                  30

Xaa Leu Xaa Ser Ser Xaa Asn Xaa Xaa Xaa Xaa His Xaa Xaa Xaa Xaa
        35                  40                  45

Xaa Xaa Xaa Xaa Xaa Xaa Xaa Xaa Xaa Xaa Met Glu
    50                  55                  60

( 2 ) INFORMATION FOR SEQ ID NO:6:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:6:

```
Asp Xaa Arg Xaa Xaa Xaa Xaa Ile Xaa Ser Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Asn Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Ser
    50                  55                  60
```

( 2 ) INFORMATION FOR SEQ ID NO:7:

( i ) SEQUENCE CHARACTERISTICS:
    ( A ) LENGTH: 61 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:7:

```
Xaa Pro Xaa Xaa Ser Xaa Thr Ala Xaa Xaa Xaa Gln Xaa Val Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Thr Xaa Xaa Xaa Ser Xaa Xaa Xaa Val Xaa Xaa
        35                  40                  45

Xaa Xaa Xaa Xaa Xaa Xaa Xaa Xaa Xaa Xaa Xaa Asp His
    50                  55                  60
```

( 2 ) INFORMATION FOR SEQ ID NO:8:

( i ) SEQUENCE CHARACTERISTICS:
    ( A ) LENGTH: 61 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:8:

```
Gln Pro Asn Ala Val Xaa Thr Asn Phe Xaa Thr Lys Xaa Leu Thr Xaa
1               5                   10                  15

Xaa Xaa Xaa Xaa Xaa Xaa Xaa Xaa Lys Xaa Xaa Xaa Xaa Ala Xaa Xaa
            20                  25                  30

Val Xaa Xaa Xaa Ala Ser Xaa Gln Xaa Asn Xaa Thr Xaa Val Xaa Xaa
        35                  40                  45
```

```
Xaa  Xaa  Xaa  Xaa  Xaa  Xaa  Xaa  Xaa  Gln  Xaa  Xaa  Arg  Glu
     50                       55                  60
```

( 2 ) INFORMATION FOR SEQ ID NO:9:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

```
Xaa  Pro  Xaa  Xaa  Ser  Xaa  Thr  Ala  Xaa  Xaa  Xaa  Gln  Xaa  Val  Xaa  Xaa
1                   5                        10                       15

Xaa  Xaa  Xaa  Xaa  Xaa  Xaa  Tyr  Xaa  Xaa  Xaa  Xaa  Xaa  Xaa  Xaa  Xaa
               20                  25                       30

Val  Xaa  Xaa  Xaa  Xaa  Xaa  Xaa  Xaa  Ser  Xaa  Xaa  Xaa  Xaa  Xaa
          35                       40                  45

Xaa  Xaa  Xaa  Xaa  Xaa  Xaa  Xaa  Xaa  Xaa  Xaa  Xaa  Asp  His
     50                       55                       60
```

( 2 ) INFORMATION FOR SEQ ID NO:10:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:10:

```
Thr  Lys  Asp  Lys  Tyr  Xaa  Val  Val  Xaa  Xaa  Asp  His  Xaa  Arg  Xaa  Xaa
1                   5                        10                       15

Xaa  Xaa  Xaa  Xaa  Xaa  Xaa  Tyr  Ser  Xaa  Xaa  Ile  Xaa  Ile  Xaa  Xaa  Lys
               20                  25                       30

Ala  Xaa  Leu  Xaa  Ala  Thr  Xaa  Gly  Xaa  Ser  Xaa  Xaa  Xaa  Val  Xaa  Xaa
          35                       40                  45

Xaa  Xaa  Xaa  Xaa  Xaa  Xaa  Ala  Xaa  Glu  Arg  Xaa  Ile  Xaa
     50                       55                       60
```

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

CTGATTGCAT ATTAATTCTC AGAT 24

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

GATCTGAGTA ATTAATCATG CACC 24

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

TTTTGCGAGG CTAATGGTGC GTAA 24

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

AGACCAAATA ATCTTGCCTT CACT 24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

TTGTTAATAA TCTAATTACC CTAG 24

( 2 ) INFORMATION FOR SEQ ID NO:16:

( i ) SEQUENCE CHARACTERISTICS:
   ( A ) LENGTH: 37 amino acids
   ( B ) TYPE: amino acid
   ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

Xaa Xaa Xaa Xaa Xaa Xaa Leu Xaa Xaa Lys Xaa Ile Ser Xaa Pro Xaa
1               5                   10                  15
Xaa Val Xaa Leu Xaa Val Met Xaa Asn Xaa Xaa Xaa Xaa His Xaa Xaa
            20              25                      30
Xaa Xaa Xaa Xaa Xaa
            35

( 2 ) INFORMATION FOR SEQ ID NO:17:

( i ) SEQUENCE CHARACTERISTICS:
      ( A ) LENGTH: 37 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:17:

Xaa Xaa Xaa Xaa Xaa Xaa Xaa Cys Xaa Arg Xaa Ile Xaa Ile Xaa Xaa
1               5                   10                  15
Lys Ser Xaa Leu Xaa Val Asn Xaa Gly Xaa Ser Xaa Xaa Xaa Val Xaa
            20              25                      30
Xaa Xaa Xaa Xaa Xaa
            35

( 2 ) INFORMATION FOR SEQ ID NO:18:

( i ) SEQUENCE CHARACTERISTICS:
      ( A ) LENGTH: 37 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:18:

Xaa Xaa Xaa Xaa Xaa Xaa Glu Thr Gln Lys Xaa Xaa Ser Pro Pro Glu
1               5                   10                  15
Xaa Lys Arg Leu Xaa Lys Met Xaa Gln Xaa Ser Xaa Xaa Xaa Val Xaa
            20              25                      30
Xaa Xaa Xaa Xaa Xaa
            35

-continued ( 2 ) INFORMATION FOR SEQ ID NO:19:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:19:

```
Xaa Xaa Xaa Xaa Xaa Xaa Xaa Cys Lys Lys Xaa Xaa Ser Leu Thr Glu
  1               5                  10                  15
Xaa Ser Gln Xaa Xaa Xaa Xaa Xaa Lys Xaa Ser Xaa Val Xaa Val Xaa
         20                  25                  30
Xaa Xaa Xaa Xaa Xaa
         35
```

( 2 ) INFORMATION FOR SEQ ID NO:20:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:20:

```
Xaa Xaa Xaa Xaa Xaa Xaa Xaa Tyr Ser Xaa Xaa Ile Xaa Ile Xaa Xaa
  1               5                  10                  15
Lys Ala Xaa Leu Xaa Ala Thr Xaa Gly Xaa Ser Xaa Xaa Xaa Val Xaa
         20                  25                  30
Xaa Xaa Xaa Xaa Xaa
         35
```

( 2 ) INFORMATION FOR SEQ ID NO:21:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:21:

```
Xaa Xaa Xaa Xaa Xaa Xaa Xaa Tyr Ser Xaa Xaa Ile Xaa Ile Xaa Xaa
  1               5                  10                  15
Lys Ser Xaa Leu Xaa Ala Asn Xaa Gly Xaa Xaa Xaa Xaa Xaa Val Xaa
         20                  25                  30
Xaa Xaa Xaa Xaa Xaa
         35
```

( 2 ) INFORMATION FOR SEQ ID NO:22:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:22:

```
Xaa Xaa Xaa Xaa Xaa Xaa Leu Xaa Xaa Pro Xaa Xaa Xaa Xaa Lys Xaa
1               5                   10                  15
Xaa Xaa Xaa Val Ser Xaa Thr Xaa Gly Xaa Xaa Xaa Xaa Xaa Val Xaa
            20              25                      30
Xaa Xaa Xaa Xaa Xaa
            35
```

( 2 ) INFORMATION FOR SEQ ID NO:23:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:23:

```
Xaa Xaa Xaa Xaa Xaa Xaa Xaa Xaa Xaa Lys Xaa Xaa Cys Xaa Pro Xaa
1               5                   10                  15
Xaa Val Xaa Xaa Xaa Ala Leu Xaa Asp Xaa Xaa Xaa Xaa Xaa Val Xaa
            20              25                      30
Xaa Xaa Xaa Xaa Xaa
            35
```

( 2 ) INFORMATION FOR SEQ ID NO:24:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:24:

```
Xaa Xaa Xaa Xaa Xaa Xaa Xaa Xaa Xaa Xaa Xaa Xaa Cys Xaa Pro Xaa
1               5                   10                  15
Xaa Val Xaa Met Xaa Asn Leu Xaa Asn Xaa Xaa Xaa Xaa Xaa Xaa Xaa
            20              25                      30
Xaa Xaa Xaa Xaa Xaa
            35
```

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:25:

GATCCTTGTT AATCTAATTA CCCTAGGTCT AA        32

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

GATCCCTGAT TGCATATTAA TTCTCAGATA        30

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:27:

GATCCGATCT CAGTAATTAA TCATGCACCA        30

( 2 ) INFORMATION FOR SEQ ID NO:28:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:28:

GATCCGCGAG GCTAATGGTG CGTAAAAGCA CTGGTGA        37

( 2 ) INFORMATION FOR SEQ ID NO:29:

(  i  ) SEQUENCE CHARACTERISTICS:
    (  A  ) LENGTH: 24 base pairs
    (  B  ) TYPE: nucleic acid
    (  C  ) STRANDEDNESS: single
    (  D  ) TOPOLOGY: linear (  i i  ) MOLECULE TYPE: cDNA (  i i i  ) HYPOTHETICAL: NO (  i v  ) ANTI-SENSE: NO (  x i  ) SEQUENCE DESCRIPTION: SEQ ID NO:29:

GATCCAGGCA AGATTATTTG GTCA 24